United States Patent
Long et al.

(10) Patent No.: US 7,924,163 B1
(45) Date of Patent: Apr. 12, 2011

(54) CORDLESS PATIENT PAD

(75) Inventors: Timothy G. Long, Novato, CA (US);
Steven A. Williams, Discovery Bay (HK)

(73) Assignee: Smart Caregiver Corporation, Petaluma, CA (US)

( * ) Notice: Subject to any disclaimer, the term of this patent is extended or adjusted under 35 U.S.C. 154(b) by 290 days.

(21) Appl. No.: 12/189,732

(22) Filed: Aug. 11, 2008

Related U.S. Application Data

(60) Provisional application No. 60/954,892, filed on Aug. 9, 2007.

(51) Int. Cl.
*G08B 21/00* (2006.01)

(52) U.S. Cl. ...................................... 340/573.1; 340/666

(58) Field of Classification Search ................ 340/573.1, 340/666, 667, 612, 614, 626
See application file for complete search history.

(56) References Cited

U.S. PATENT DOCUMENTS

| | | | | |
|---|---|---|---|---|
| 4,633,237 A | * | 12/1986 | Tucknott et al. | 340/573.4 |
| 5,410,297 A | | 4/1995 | Joseph | |
| 5,654,694 A | | 8/1997 | Newham | |
| 5,808,552 A | * | 9/1998 | Wiley et al. | 340/573.4 |
| 6,067,019 A | * | 5/2000 | Scott | 340/573.4 |
| 6,078,261 A | * | 6/2000 | Davsko | 340/573.4 |
| 6,583,727 B2 | * | 6/2003 | Nunome | 340/665 |
| 6,778,090 B2 | * | 8/2004 | Newham | 340/573.1 |
| 7,253,366 B2 | * | 8/2007 | Bhai | 177/45 |
| 7,598,853 B2 | * | 10/2009 | Becker et al. | 340/539.13 |
| 7,656,299 B2 | * | 2/2010 | Gentry et al. | 340/573.1 |
| 2007/0010719 A1 | * | 1/2007 | Huster et al. | 600/300 |
| 2009/0112626 A1 | * | 4/2009 | Talbot et al. | 705/3 |

* cited by examiner

*Primary Examiner* — Toan N Pham
(74) *Attorney, Agent, or Firm* — Craig M. Stainbrook; Stainbrook & Stainbrook, LLP

(57) ABSTRACT

A cordless pressure pad connected to a bed pad transmitter for centralized monitoring by a central bed monitor receiving and alarm unit. When a monitored person gets up from bed, the pad transmitter sends a coded RF signal matched to a particular bed monitor unit, and it then triggers an alarm; when the person sits or lays back down, the pad transmitter sends a signal to the monitor to reset. Multiple pads can be linked to a single bed monitor.

11 Claims, 22 Drawing Sheets

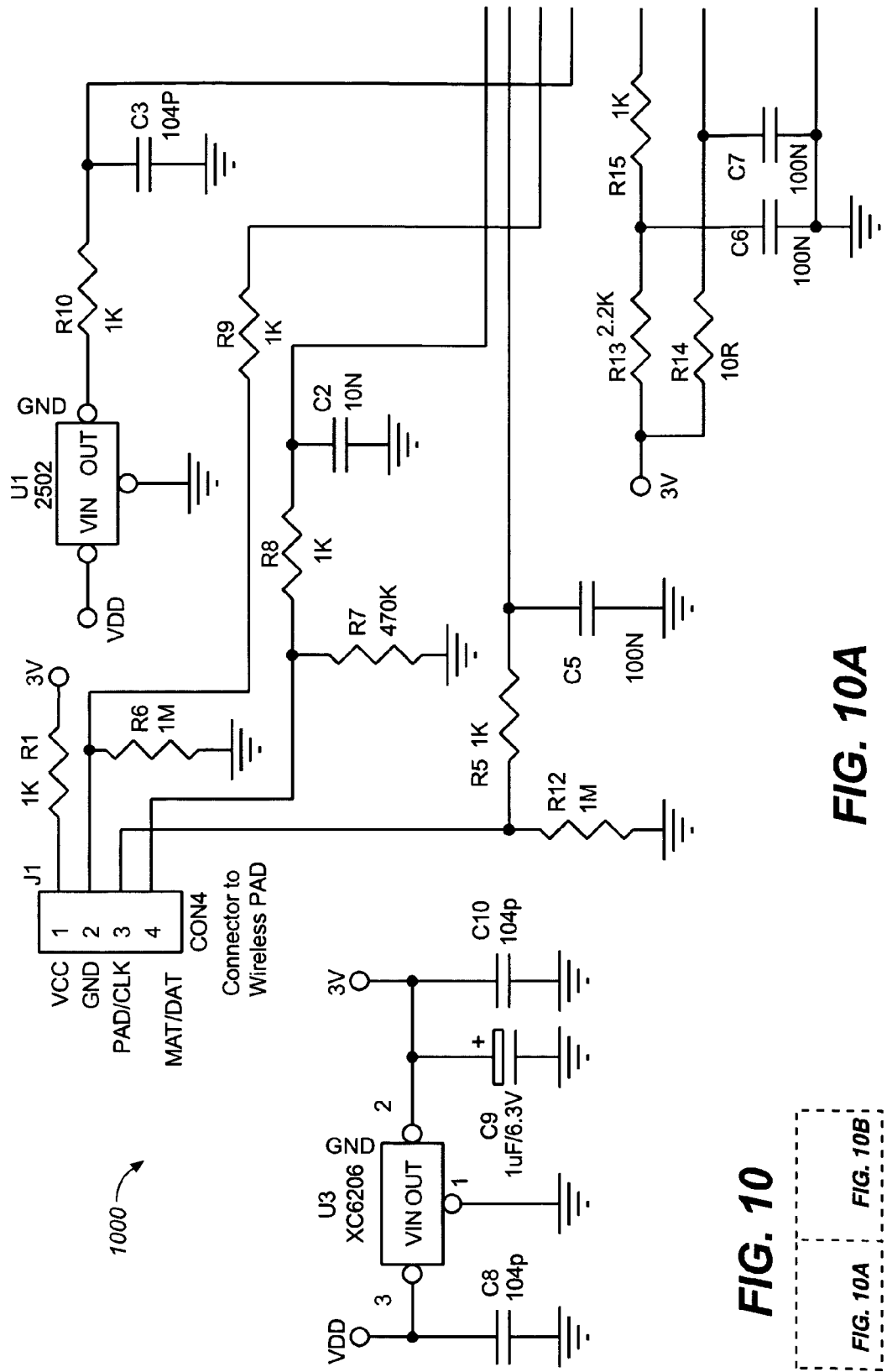

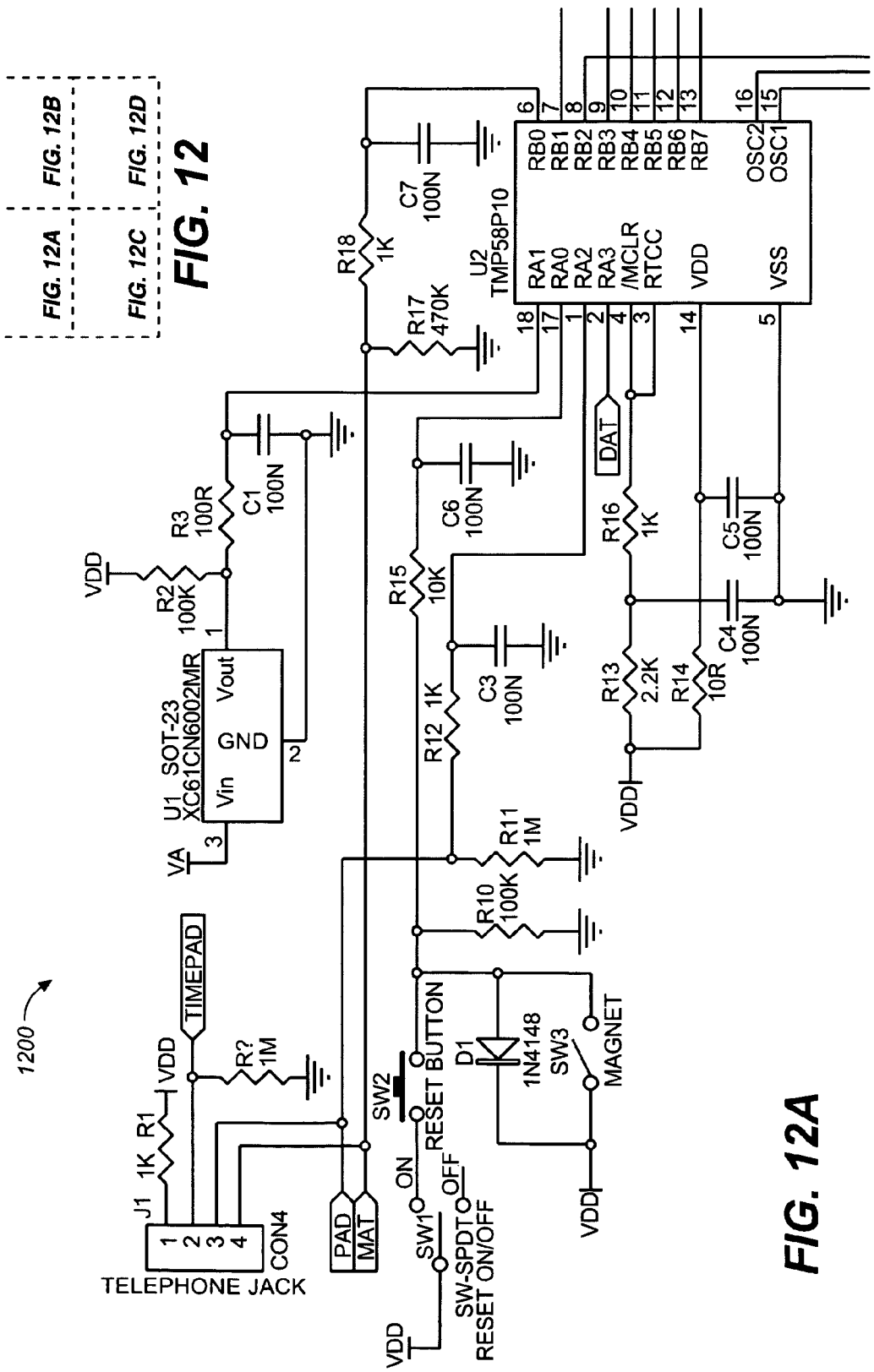

CORDLESS PATIENT PAD

CROSS REFERENCES TO RELATED APPLICATIONS

The present application claims the benefit of U.S. Provisional Patent Application Ser. No. 60/954,892, filed Aug. 9, 2007.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

Cordless or wireless pad used on a bed to monitor if a person gets or falls out of bed.

2. Discussion of Related Art Including Information Disclosed Under 37 CFR 1.97, 1.98

Residential care facilities, particularly long-term residential care nursing facilities, must provide a considerable measure of protection to residents who may be impaired in their ability to care for themselves or to exercise sound judgment Inherent in such care is the need to routinely confine residents to beds, chairs, or other support apparatus. Accordingly, it is known to provide bed and chair occupancy monitoring systems to alert staff or attendants of inappropriate patient movement.

For example, U.S. Pat. No. 5,410,297 to Joseph teaches a bed monitoring system including a capacitive sensor pad for placement under a patient. The pad comprises a foam plastic pad and heavy aluminum foil plates laminated on opposite sides of the foam. The plates are then adhesively bonded to the inner surfaces of an outer cover. The capacitor of the pad is connected in circuit with an oscillator and produces a frequency-related output. A ripple counter establishes a frequency-related output proportional to the capacitance. A microprocessor reads the counter output and samples are averaged to establish a reference base and the true weight affect of the patient on the sensing pad. Other factors which might effect the signal are readily attended to by programmed compensation. Each subsequent sample is averaged and compared with the reference base. If within a permitted range, the latest and current signal is averaged with the reference base and establishes a new base, and continuously tracks changes in the sensing system. A selected change in a selected time delay system actuates an alert or alarm system, which requires positive resetting to terminate the alarm system. The system is positively reset to return to normal position monitoring. The system may be set to automatically reset the alarm system after an alarm condition is established and then removed by the continuous tracking of the patient movement. Also illustrative of the art, U.S. Pat. No. 5,654,694 to Newham discloses a mobile patient monitoring system. The system includes a load sensor which detects the presence of a patient on a device and further includes a microprocessor responsive to a resident program. A first circuit connected to the microprocessor and to the sensor automatically activates operation of the microprocessor to a "monitor" mode upon detection by the sensor of the patient's presence on the device; it maintains operation of the microprocessor for a predetermined time period at least equal to a running time of the program; and it terminates operation of the microprocessor at the expiration of the predetermined time period after detection by the sensor of termination of the patient's presence on the device prior to expiration of the predetermined time period. A second circuit operates the system in response to commands manually applied to the second circuit to deactivate the system to a "hold/reset" mode after activating of the system to the "monitor" mode. The first circuit will also activate the system to the "monitor" mode after the system has been deactivated to the "hold/reset" mode together with subsequent detection by the sensor of termination of the patient's presence on the device and resumption of the patient's presence on the device. Alternatively, the microprocessor is responsive to the manually operable switch in the second circuit to activate the system to the "monitor" mode after the system has been deactivated to the "hold/reset" mode. A third circuit connected to the microprocessor provides an audio alarm upon demand by the microprocessor.

The present invention provides advantages over prior art systems in that the system sends a wireless signal to a remote monitor. The several advantages of the present invention are set forth below in the summary of the invention.

The foregoing patents reflect the current state of the art of which the present inventors are aware. Reference to, and discussion of, these patents is intended to aid in discharging Applicants' acknowledged duties of candor in disclosing information that may be relevant to the examination of claims to the present invention. However, it is respectfully submitted that none of the above-indicated patents disclose, teach, suggest, show, or otherwise render obvious, either singly or when considered in combination, the invention described and claimed herein.

BRIEF SUMMARY OF THE INVENTION

The present invention is a cordless or wireless pressure pad connected to a bed pad transmitter, which is in wireless communication with a proximate bed monitor. If remote or centralized monitoring is desired, the bed monitor may function as a programmable transmitter unit to relay signals from the bed pad to a central bed monitor receiving and alarm unit.

In use, the pressure pad transmits a single frequency wireless signal or wideband frequency hopping signal to the bed monitor, and if desired, to a central monitor indicating to a caregiver that a patient has gotten out of a bed or fallen out of bed. The wireless signal has a checksum to prevent faulty data, and the wireless link allows the pad to function as if a cord were connecting the pad to the user.

When triggered by the removal of a resident/patient's body weight, the pressure pad transmitter sends a coded signal that is matched with the particular bed monitor or monitors with a "self-read" in operation, and it also sends a signal outside the room directly to a monitor or light in the hall, thereby alerting caregivers to take appropriate action.

In addition, the bed pad transmitter sends a coded "I am okay" signal to the bed monitor receiver, and if the bed monitor receiver misses the pulsed signal over a predetermined and preset period, it will output an alarm signal indicating that the pad is lost or removed. This indicates that the pad has been removed from the area or is no longer working.

Each pad has a uniquely coded chip for matching with the bed monitor, and the pad is matched to the monitor by pressing a read in button on the monitor and then pressing the pad to match the codes automatically.

When a monitored person gets up from the pad the bed pad transmitter will send a signal to the bed monitor unit to trigger an alarm, and when a person sits back down the bed pad transmitter will send a signal to the bed monitor to reset the bed monitor unit.

The bed pad includes a sleeve or pocket into which the uniquely coded bed pad transmitter is inserted, and there plugged into the bed pad using a plug and socket. The pocket is closed using non-removable, tamper proof plastic clips, which must be cut to change the transmitter. The transmitter is waterproof and sealed. The battery power supply lasts more than three years and may be rechargeable.

The signal sent by the bed pad may include other functions to be decided; such as the time to change the pad (i.e., a "change pad indicator"), date manufactured, date first used, and other information to be decided.

Both units (pad and monitor) have a "low battery" circuit which send an alert signal to the bed pad monitor or central monitor. The bed monitor includes an internal wireless receiver to detect the signal from the bed pad transmitter. Alternatively, an intelligent receiver module may be plugged into the bed pad monitor wired pad port or another port as if it were a standard pad. In such a case, the external receiver unit has its own battery, indicator, sounder, and so forth, to allow the features required, such as "pad lost" indication, low battery, and the like. The battery is replaceable. However, the bed monitor receiver can work on battery and/or power supply, and may have a simple LED indicator for a "pad lost" condition with an audible sound and/or a visual output, such as an LCD light or other indicator to show in detail the functions required.

One major advantage of the wireless system of the present invention is that multiple pads can be linked to one bed monitor. This is especially well adapted for use with visual indicators, such as an LCD display. Costs are reduced because only one bed monitor receiver is required, and the alarms may be moved outside the room so as not to disturb the residents while providing a display identifying which bed is in an alarm state. Further, extra data such as pad usable time left/number of activations, and so forth, can be sent from the pad.

Other novel features which are characteristic of the invention, as to organization and method of operation, together with further objects and advantages thereof will be better understood from the following description considered in connection with the accompanying drawings, in which preferred embodiments of the invention are illustrated by way of example. It is to be expressly understood, however, that the drawings are for illustration and description only and are not intended as a definition of the limits of the invention. The various features of novelty that characterize the invention are pointed out with particularity in the claims annexed to and forming part of this disclosure. The invention does not reside in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE SEVERAL VIEWS OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
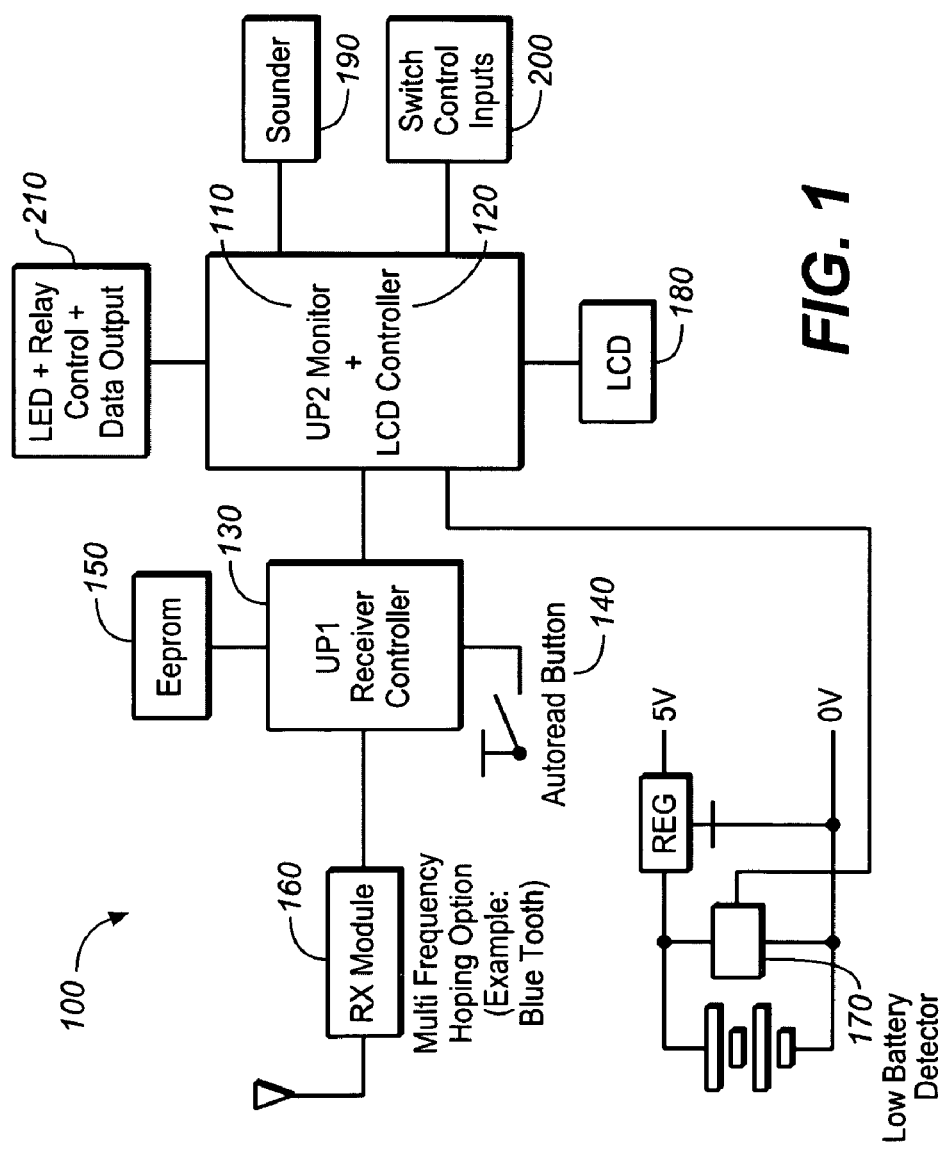
FIG. 1 is a schematic block diagram showing the functional elements of the cordless bed monitor receiving unit having an LCD display of the present invention.

Referring to FIGS. 1 through 13, wherein like reference numerals refer to like components in the various views, there is illustrated therein a new and improved wireless and cordless patient bed pad and monitor system. FIG. 1 is a schematic block diagram showing the functional elements of the cordless bed monitor receiving unit having an LCD display of the present invention, generally denominated 100 herein. It includes a monitor unit portion 110 with an LCD controller 120, a receiver controller 130 having an autoread button 140 and EEPROM 150 for reading pad transmitter information into memory, and a receiver module 160, preferably with a multi-frequency hopping option. The receiver further includes a low battery detect circuit 170, an LCD visual display 180, an audible output speaker 190, a switch for controlling inputs 200, and an LED/relay control/data output circuit portion 210.

Figure 2:
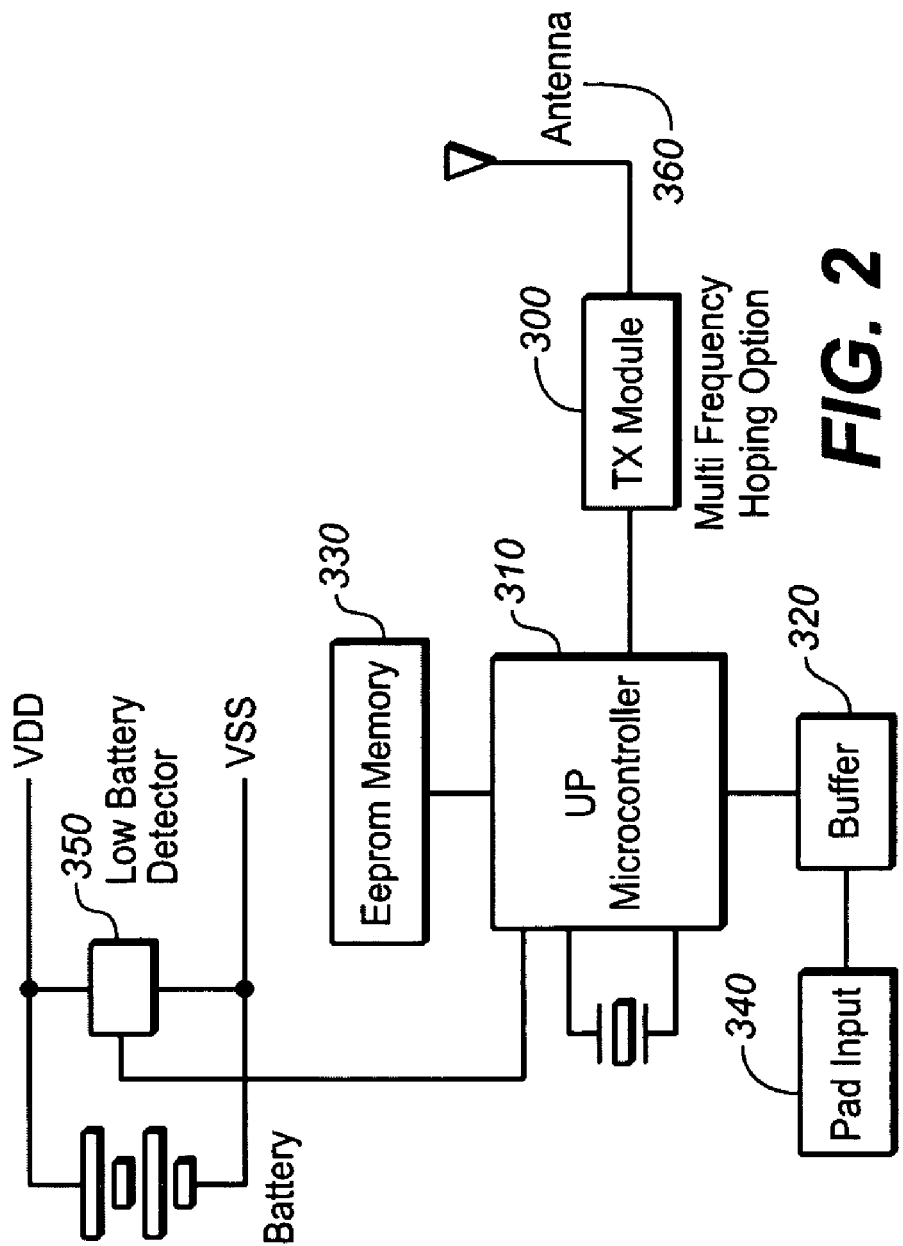
FIG. 2 is a schematic block diagram of the cordless pad transmitter unit.

FIG. 2 is a schematic block diagram of the cordless pad transmitter module 300, preferably including a multi-frequency hopping option, which comprises a microcontroller 310 having a buffer 320, EEPROM 330 for storing programmed inputs from a keypad or other input device 340, a low battery detect circuit 350, and an antenna 360 for transmitting a signal to the receiving unit shown in FIG. 1.

Figure 3:
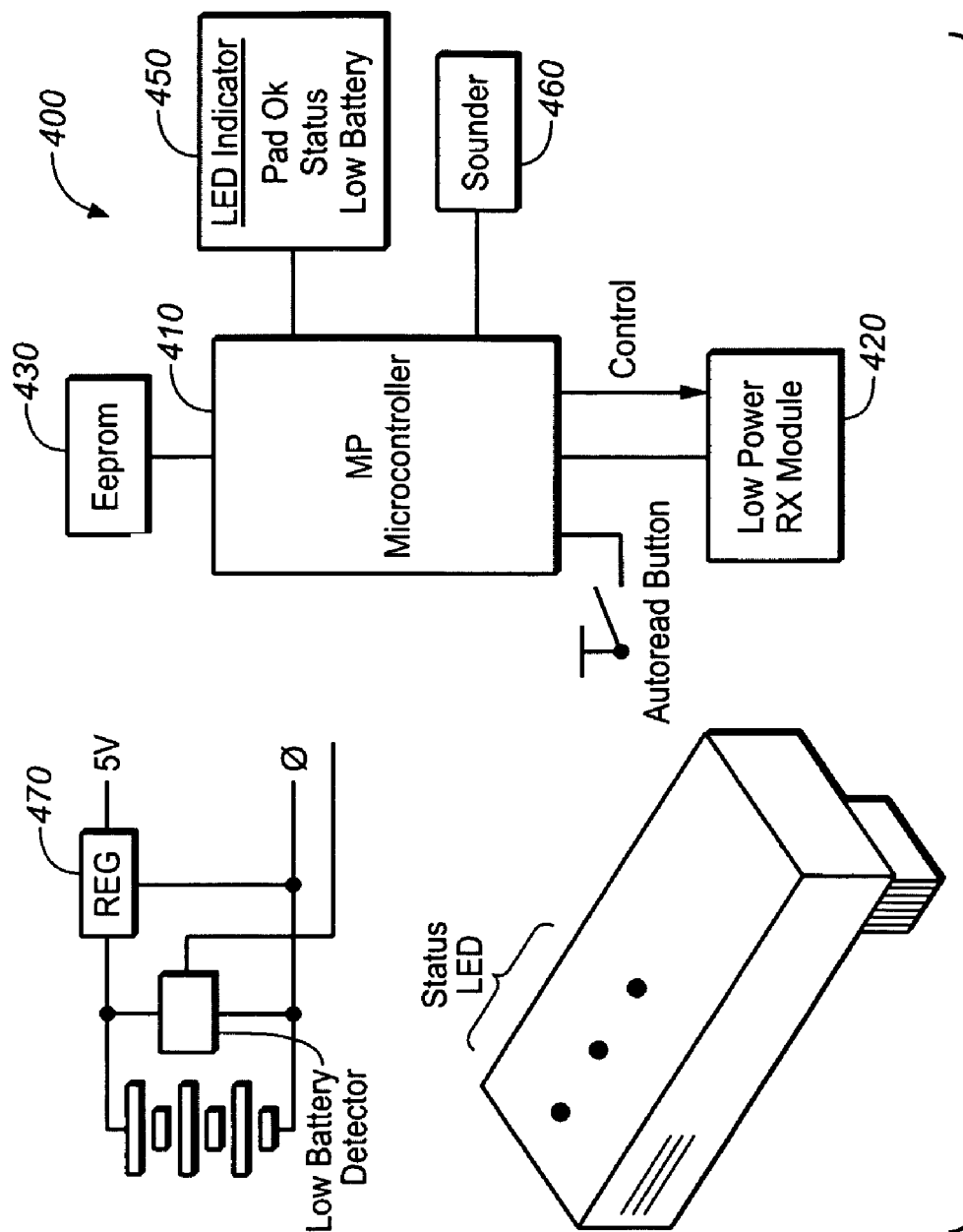
FIG. 3 is a schematic block diagram of the plug-in receiver module unit of the present invention.

FIG. 3 is a schematic block diagram of the plug-in receiver module unit 400 of the present invention, which comprises a microcontroller 410, having a low power receiver module 420, EEPROM 430, a low battery detector 440, an LED indicator 450 with indications for Pad OK, Status, and Low Battery, and an audible output device 460. Again, the unit includes an autoread button 470 for matching the unit to a bed pad transmitter.

Figure 4A:
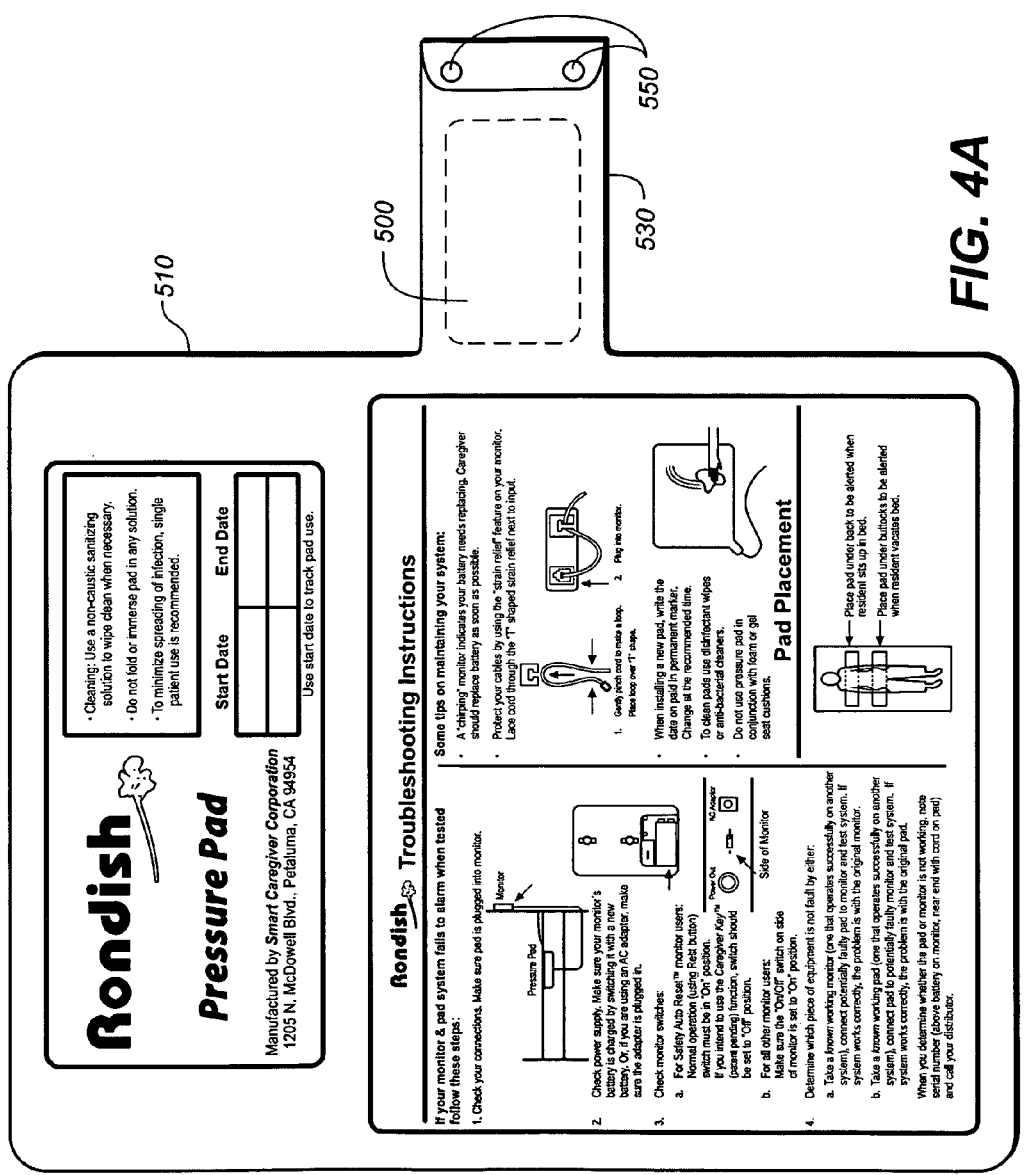
FIGS. 4A and 4B are schematic block diagrams showing how the transmitter unit is fitted and connected to the patient pad.
Figure 4B:
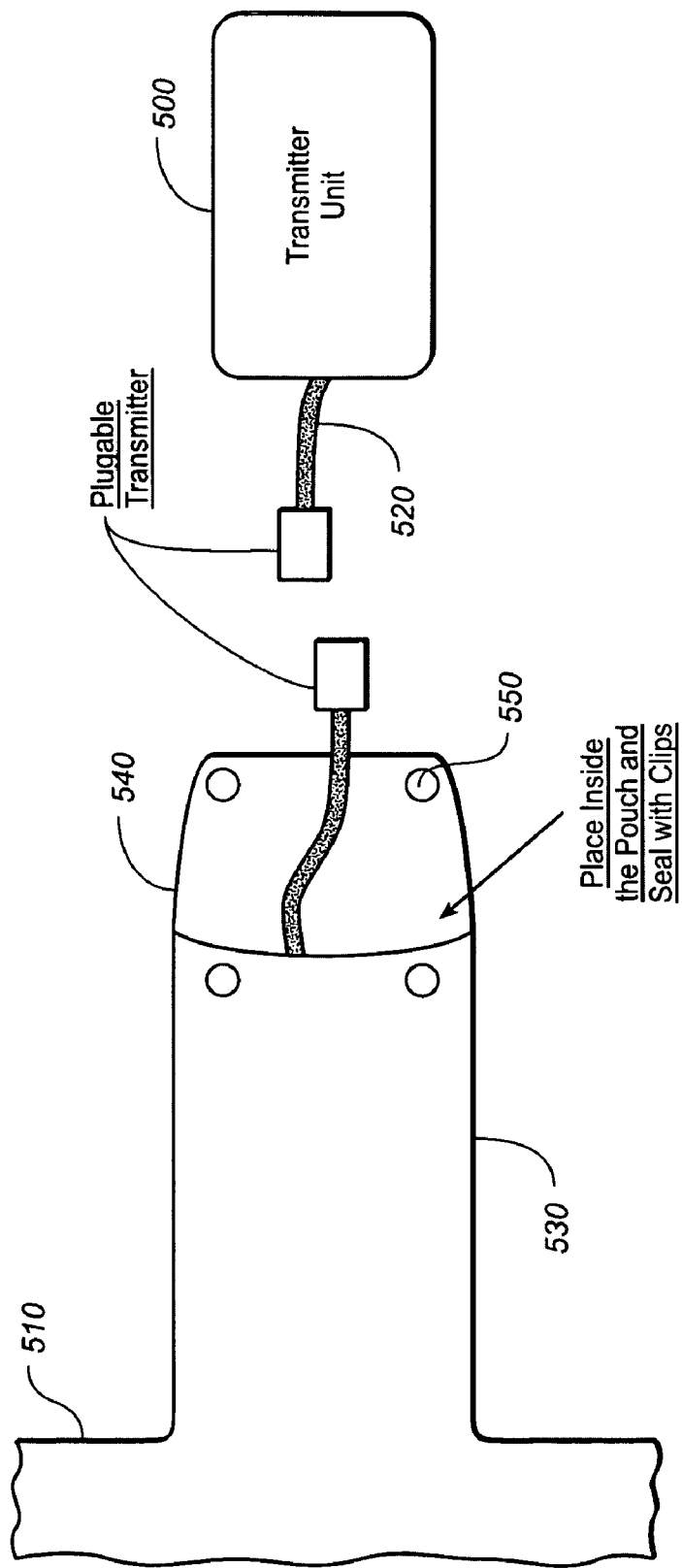

FIGS. 4A and 4B are schematic block diagrams showing how the bed pad transmitter 500 is fitted and connected to the bed pad. The transmitter is connected to the bed pad 510 with a wire connector 520, and then fitted into a pocket or sleeve 530, which is closed with a flap 540 and secured with tamper proof clips 550.

Figure 5:
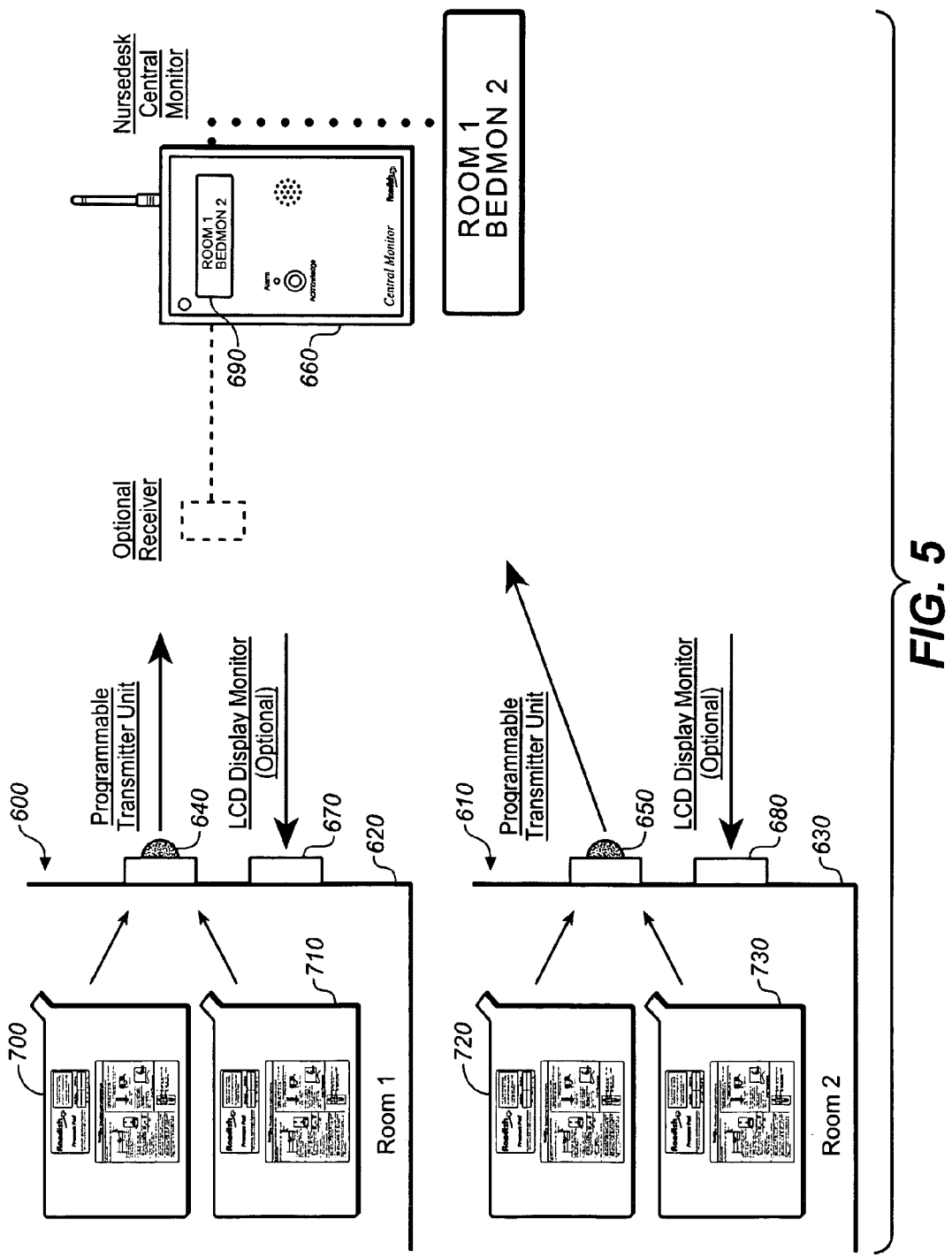
FIG. 5 is a schematic block diagram showing pad and monitor systems deployed in a number of rooms, each having dedicated transmitter units for receiving and relaying signals from bed pads to a central monitor.

FIG. 5 shows bed pad and bed pad monitor systems 600, 610, deployed in a number of rooms 620, 630, each system including dedicated transmitter units 640, 650, for receiving and relaying signals from bed pads to a central monitor 660, and an optional LCD display 670, 680 at each room. The central monitor includes a display 690 showing the room and bed pad monitor 700, 710, 720, 730 that is sending a present signal.

Figure 6:
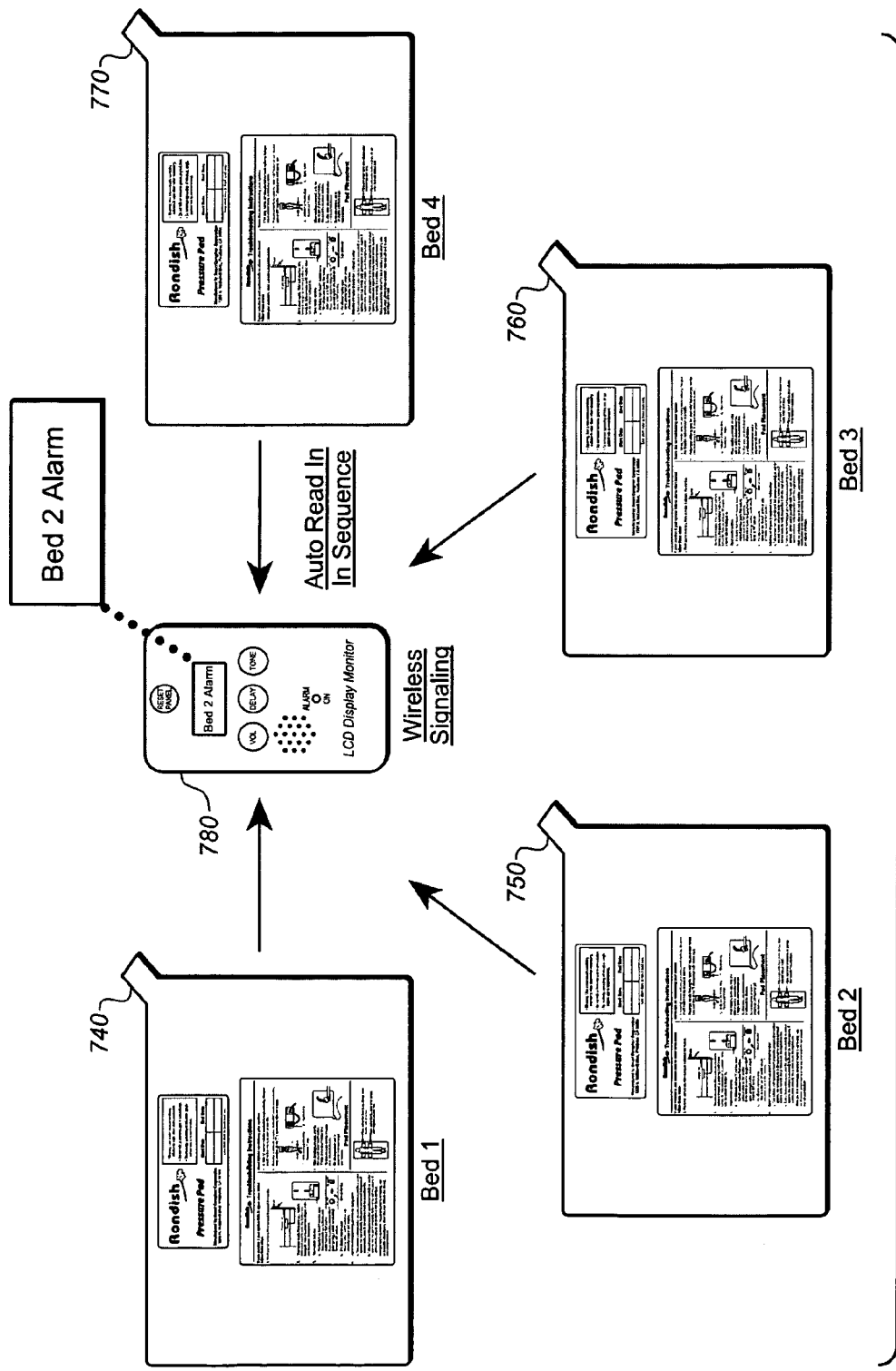
FIG. 6 similarly shows a multi-pad system, but all bed pad transmitters send signals to a single monitor.
Figure 7:
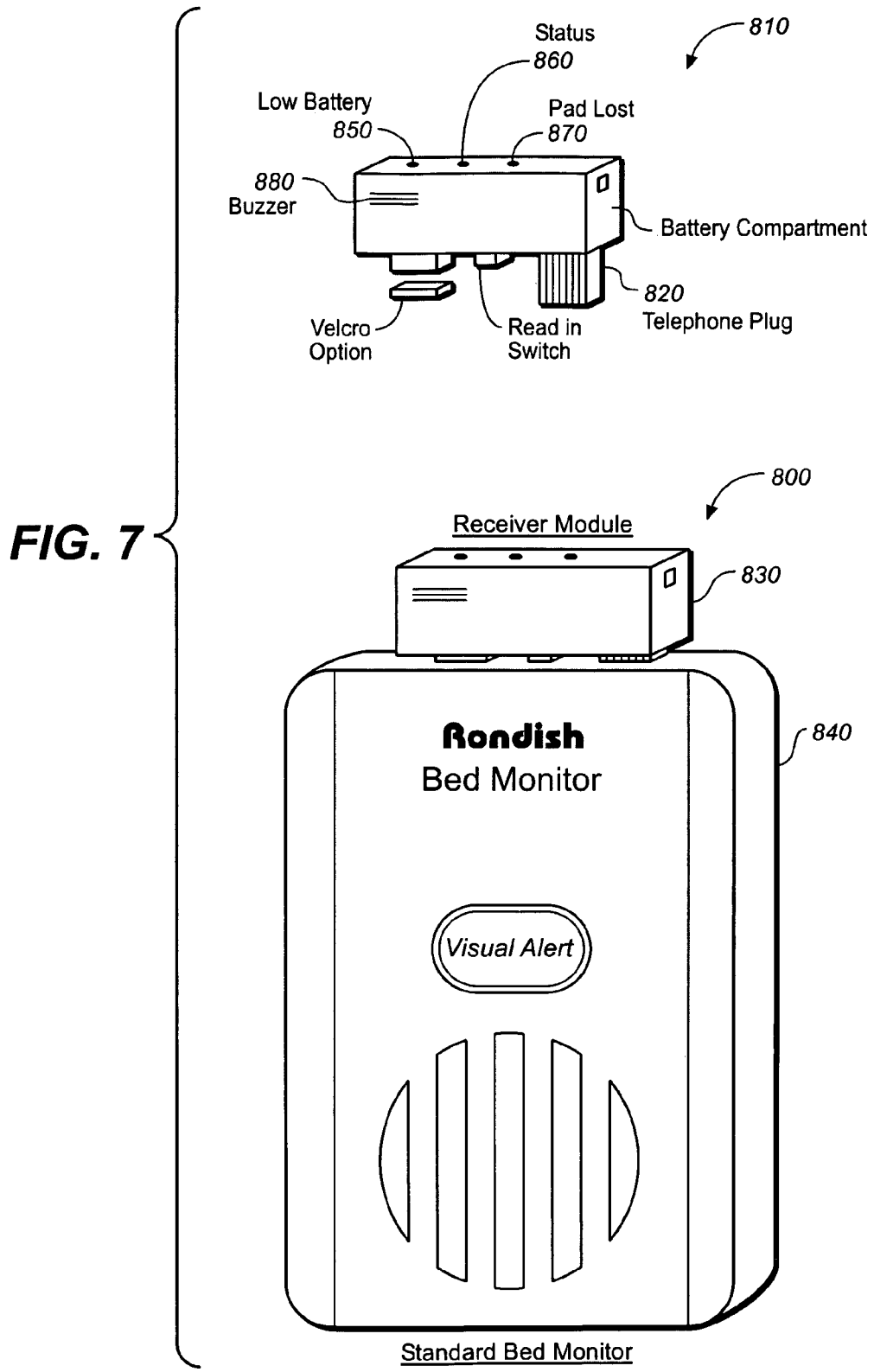
FIG. 7 is a perspective view showing the operative elements of the bed monitor receiver unit with an externally disposed receiver module.

FIG. 6 similarly shows a multi-pad system, but all bed pad transmitters 740, 750, 760, 770, send signals to a single monitor 780;

FIG. 7 is a perspective view showing the operative elements of the bed monitor receiver 800 unit with an externally disposed receiver module 810. As earlier noted, it will be appreciated that receiver circuitry can be incorporated into the receiver housing or optionally disposed in a plug-in form having a male element 820 for insertion into a female receptacle 830 in the bed monitor receiver housing 840. The receiver module is battery powered and preferably includes three indicator lights, including low battery 850, status 860, and pad lost 870, as well as a buzzer alarm output 880.

Figure 8:
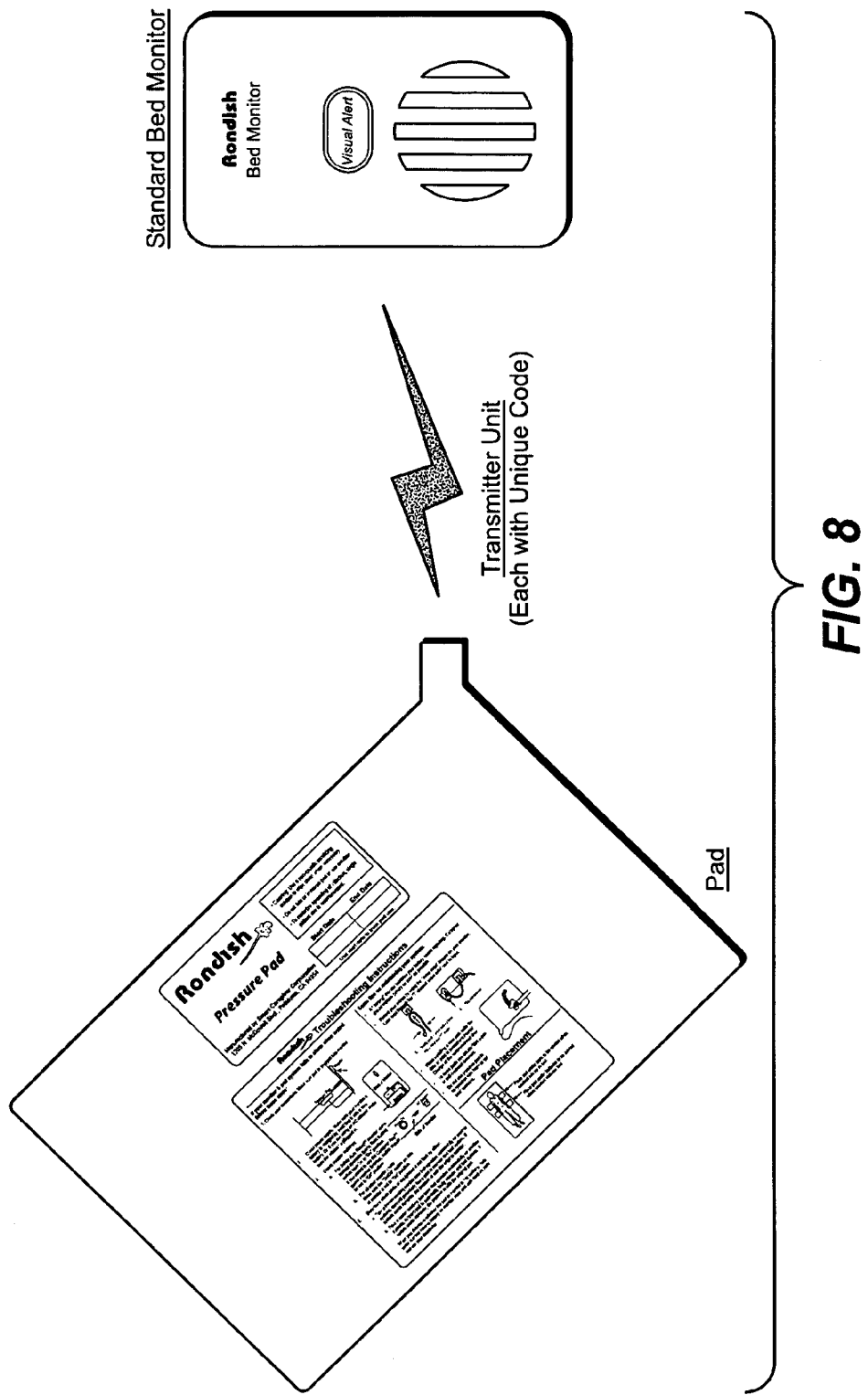
FIG. 8 is a schematic diagram showing a pad and standard receiver pair.
Figure 9:
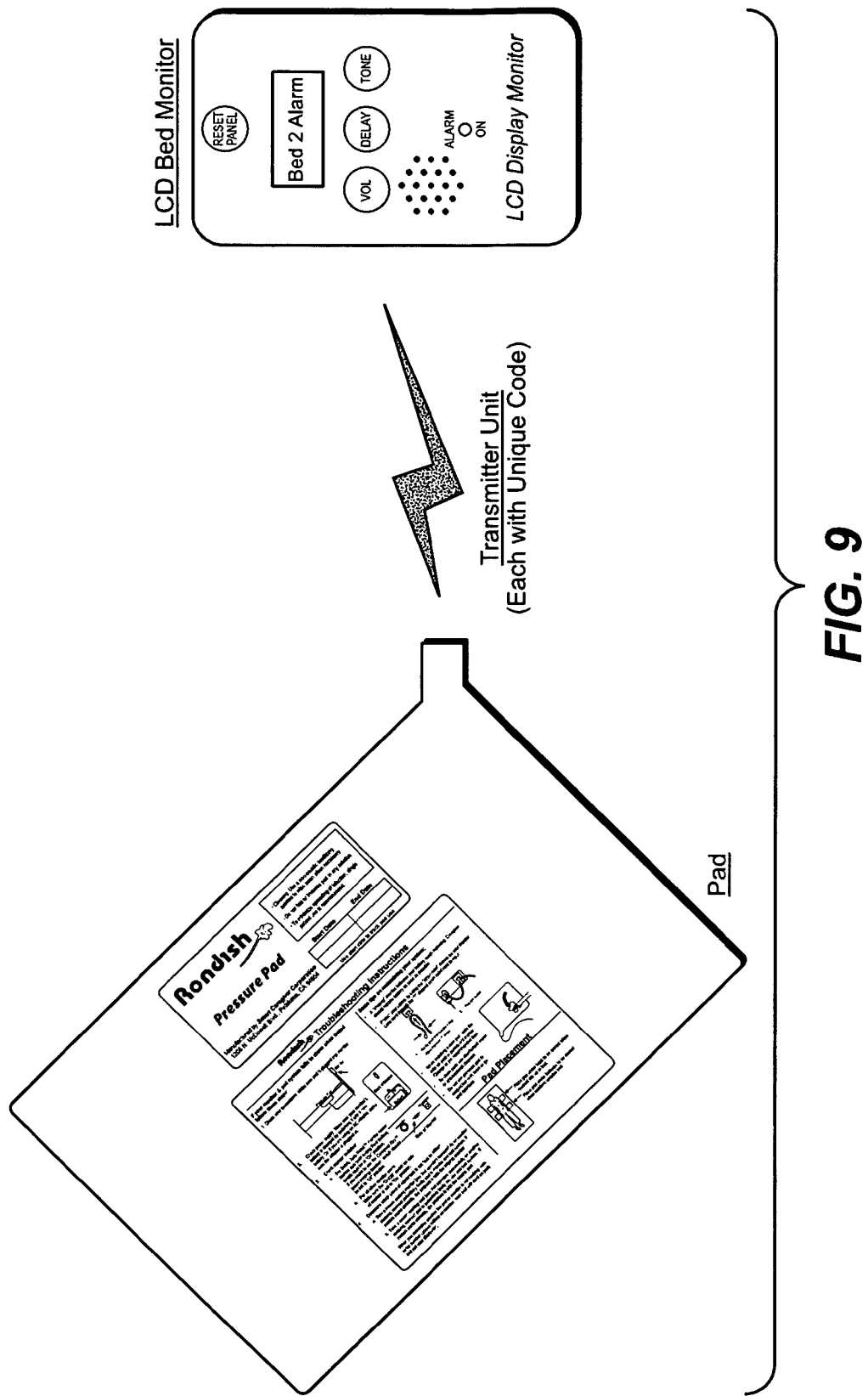
FIG. 9 is a schematic diagram showing a pad and bed monitor with an LCD display.

FIGS. 8 and 9 show pad and receiver pairs, the former with a standard receiver 890, the latter with an LCD display receiver 900.

Figure 10B:
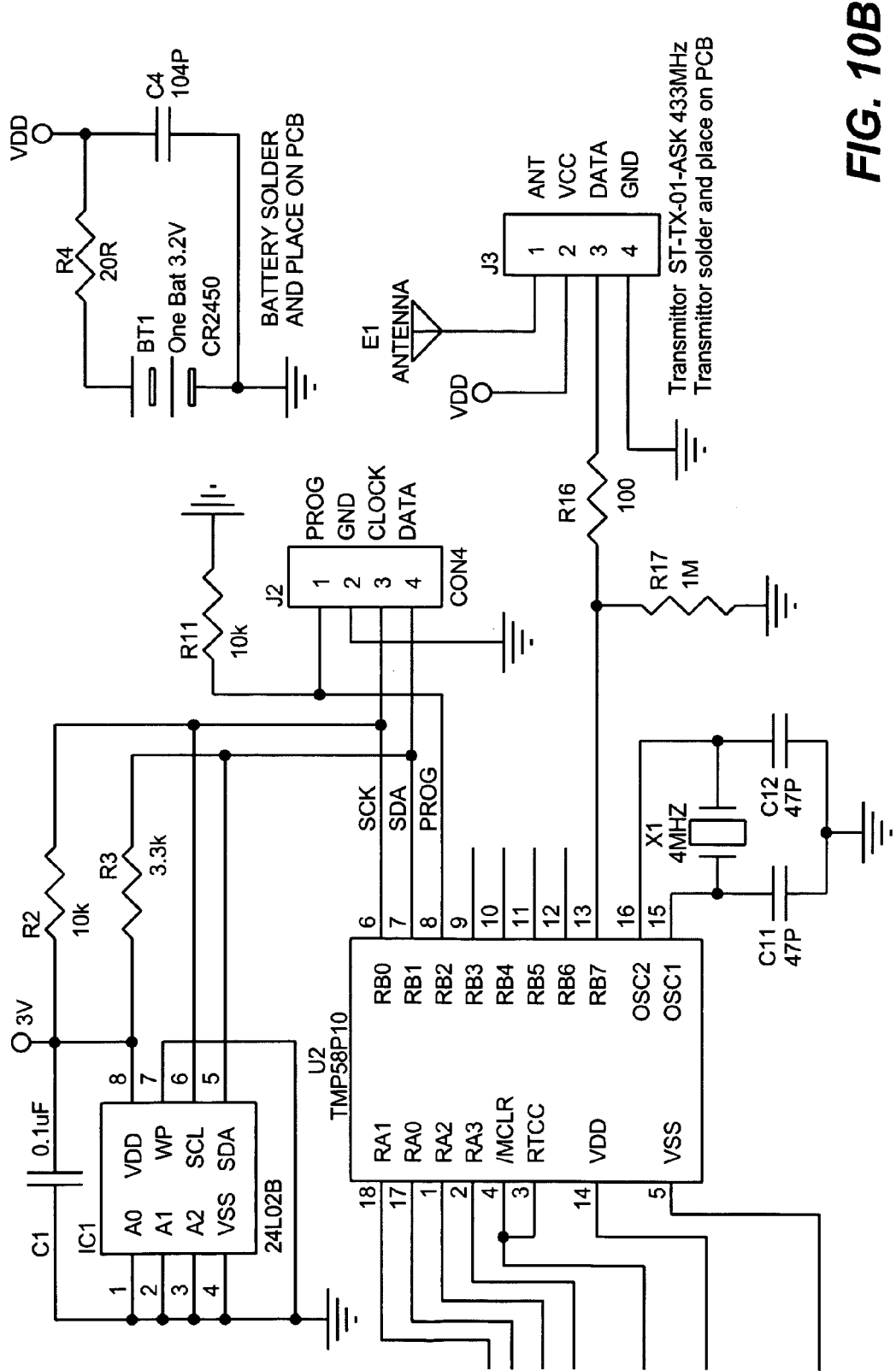
FIG. 10 is a circuit diagram of the wireless pad transmitter.
Figure 11A:
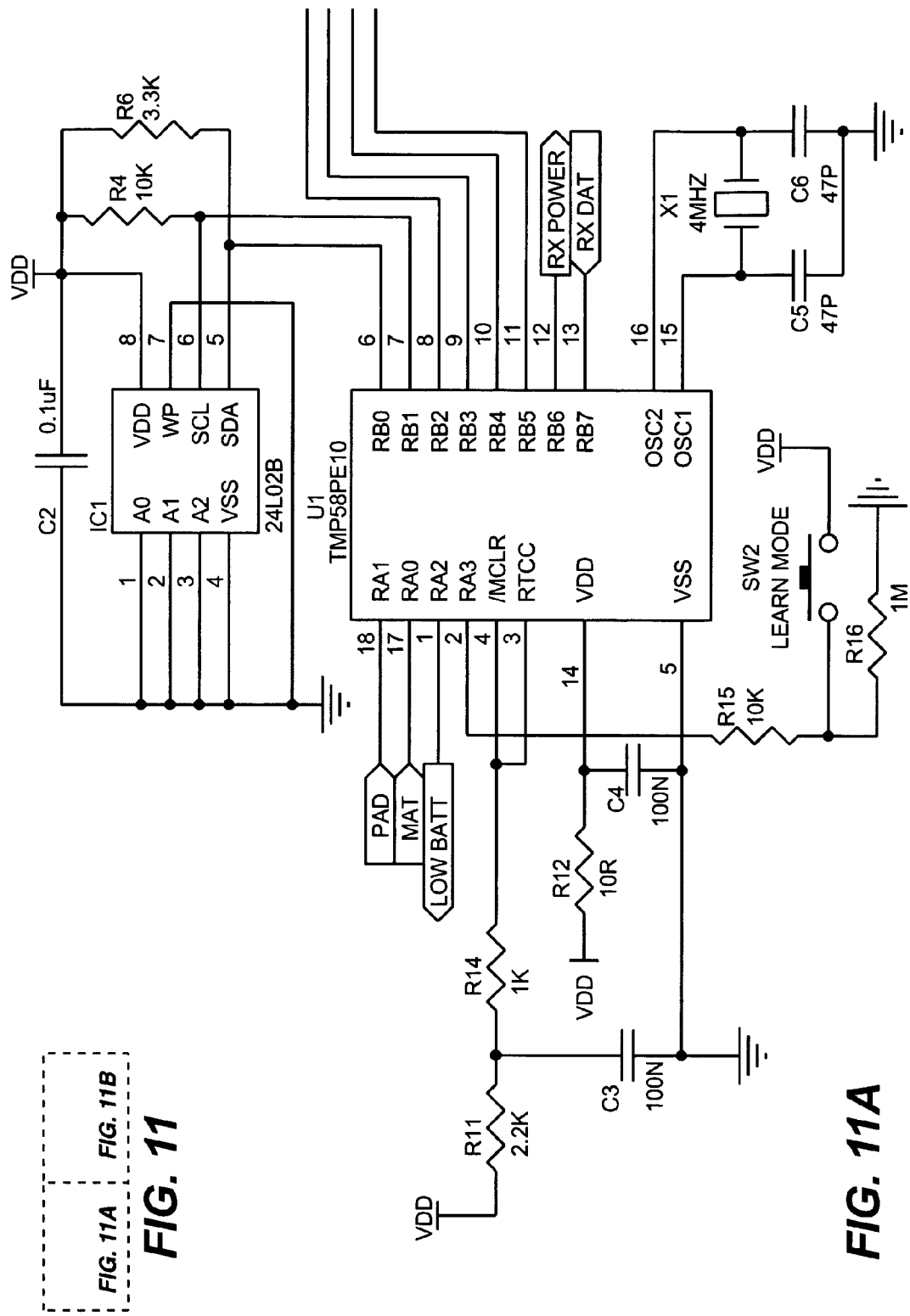
FIG. 11 is a circuit diagram of the wireless bed pad receiver unit.
Figure 11B:
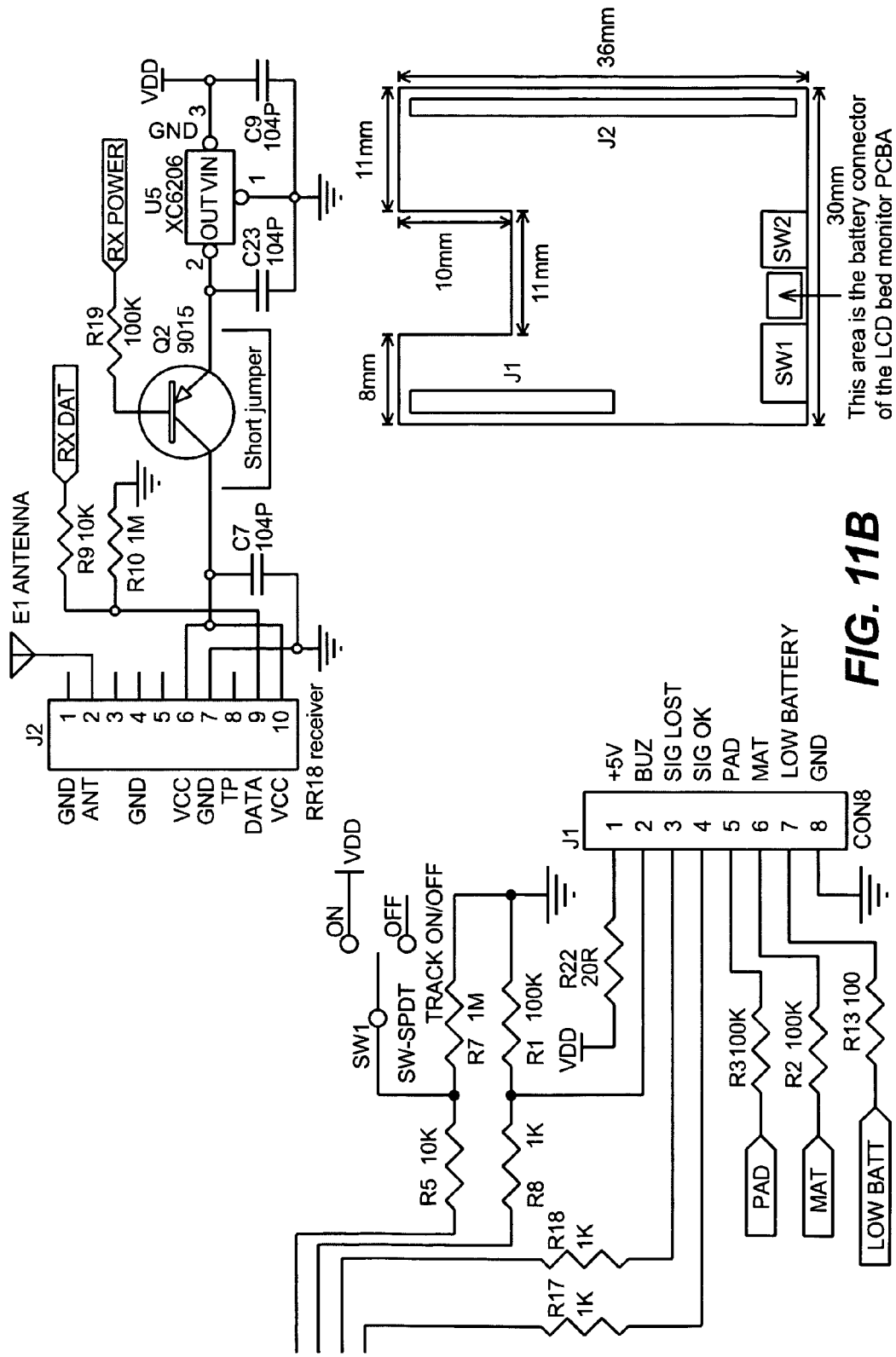
Figure 12B:
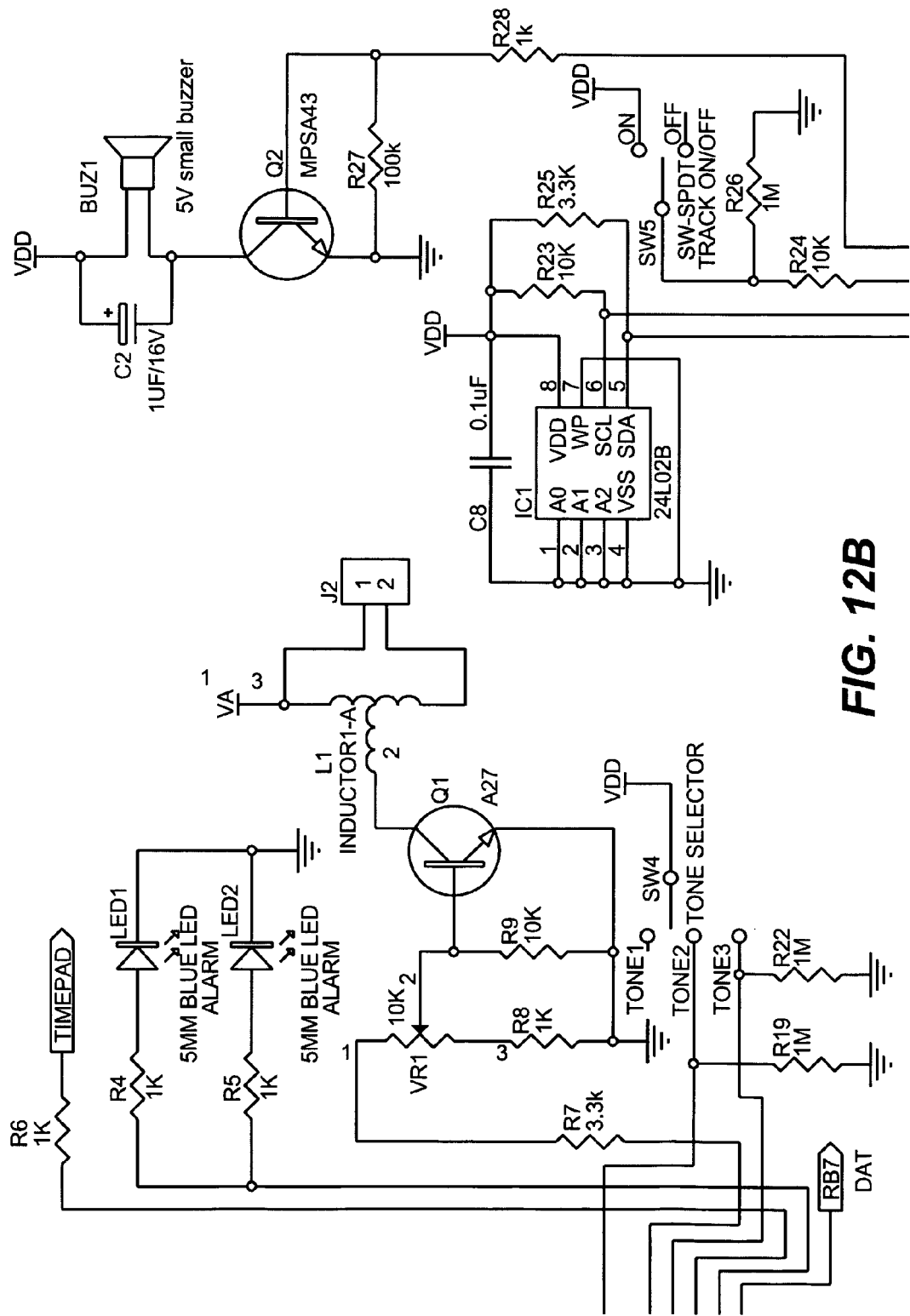
FIG. 12 is a circuit diagram of the bed pad monitor of the present invention.
Figure 12C:
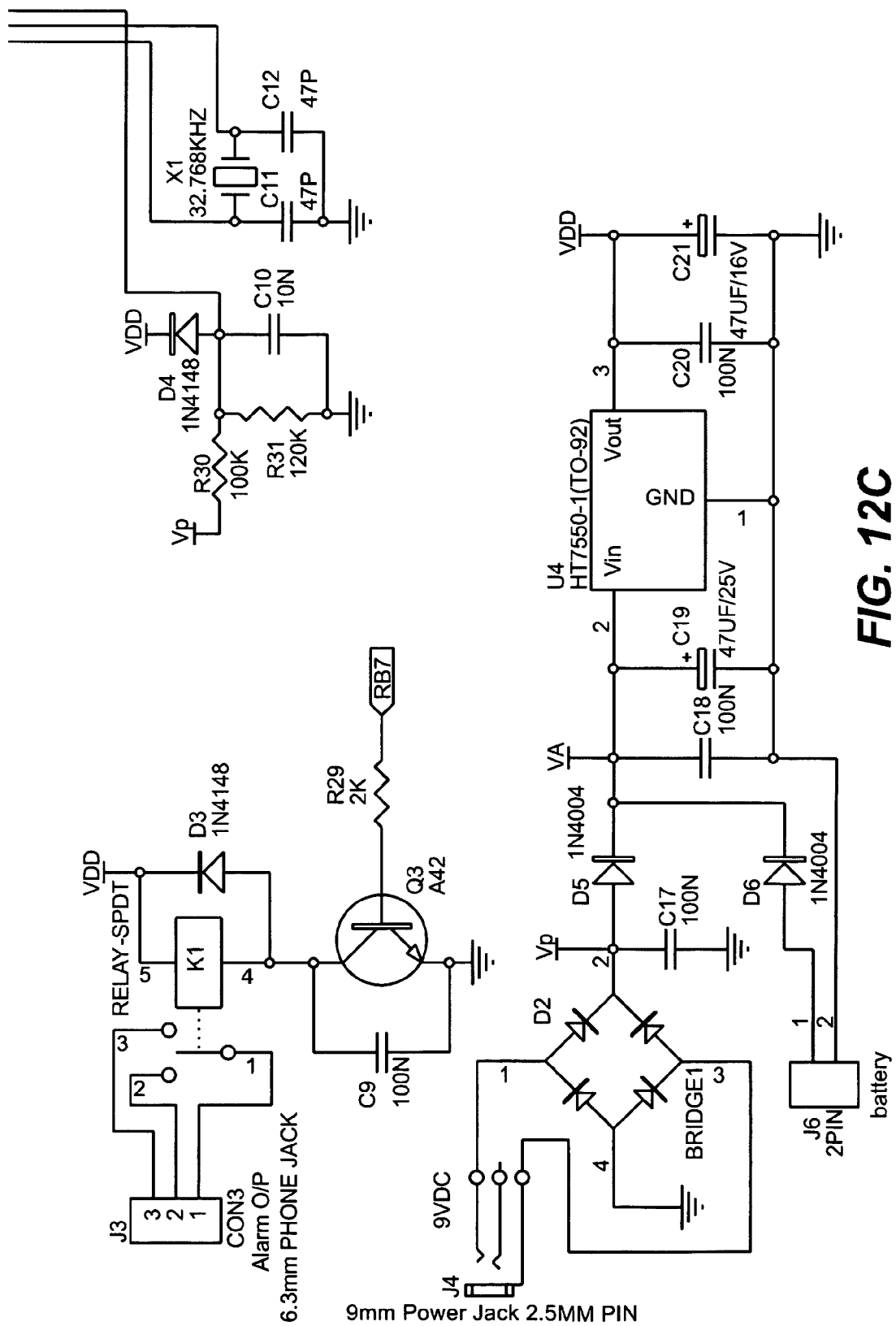
Figure 12D:
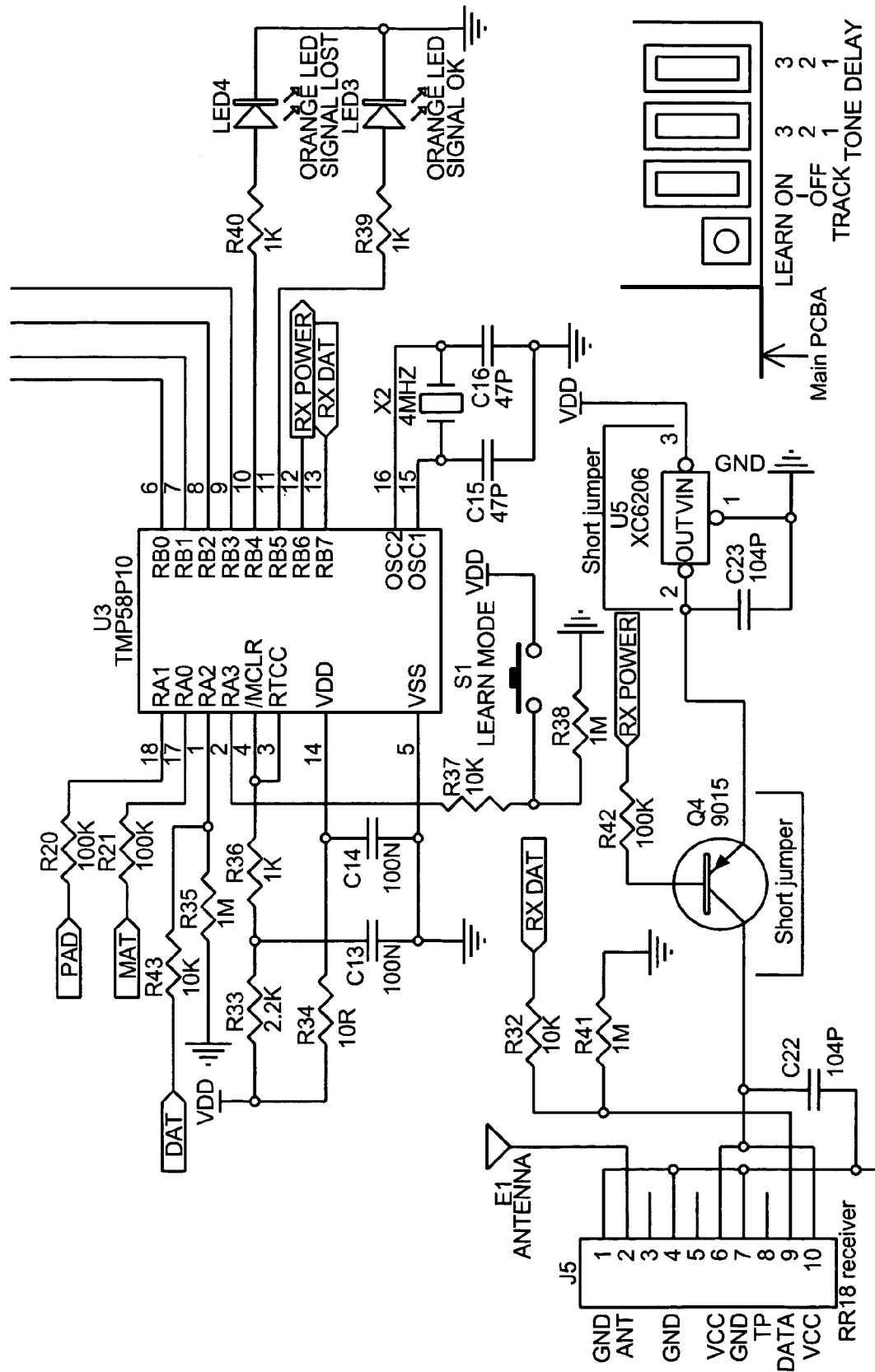
Figure 13A:
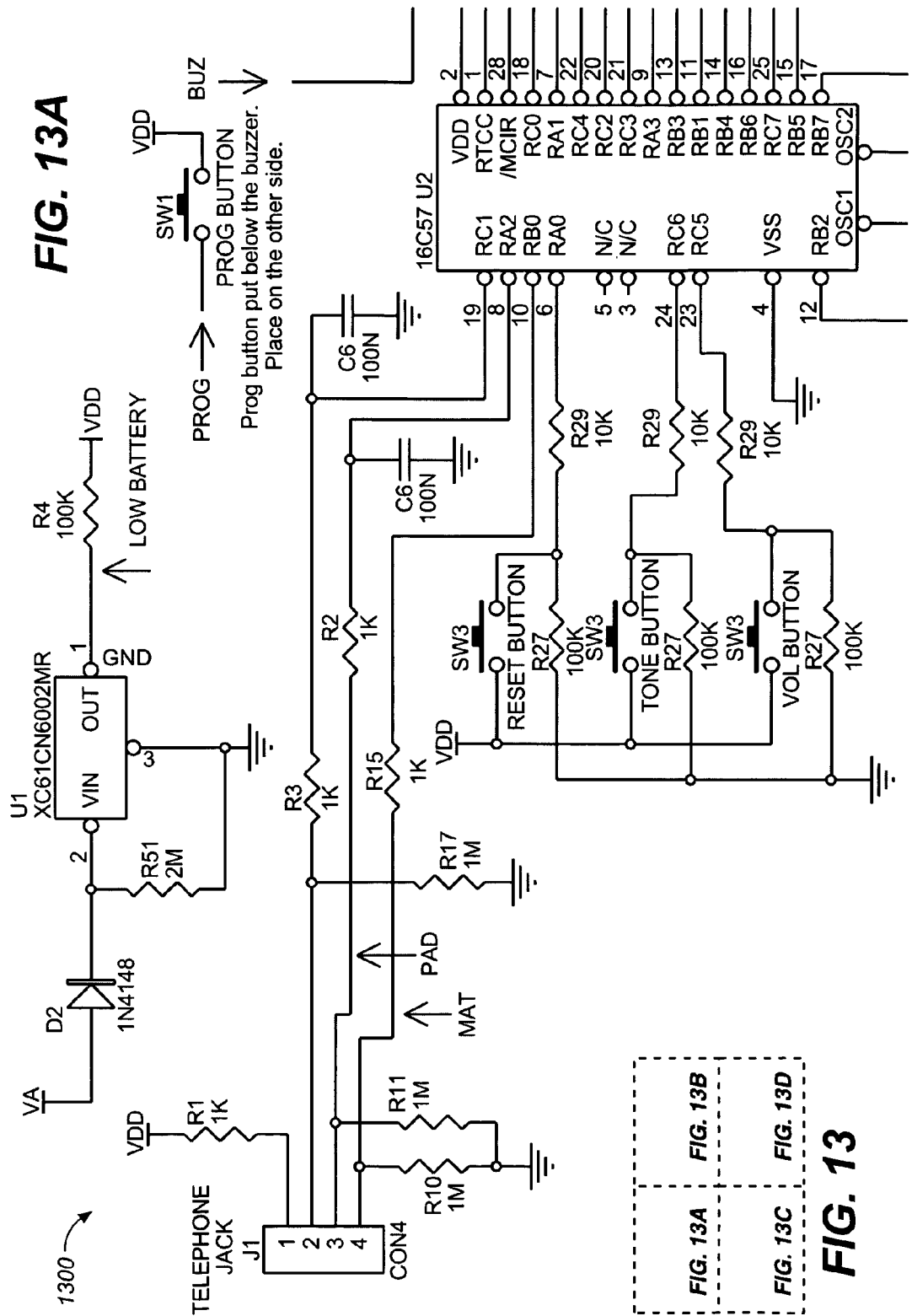
FIG. 13 is a circuit diagram of the wireless bad pad monitor having an LCD display.
Figure 13B:
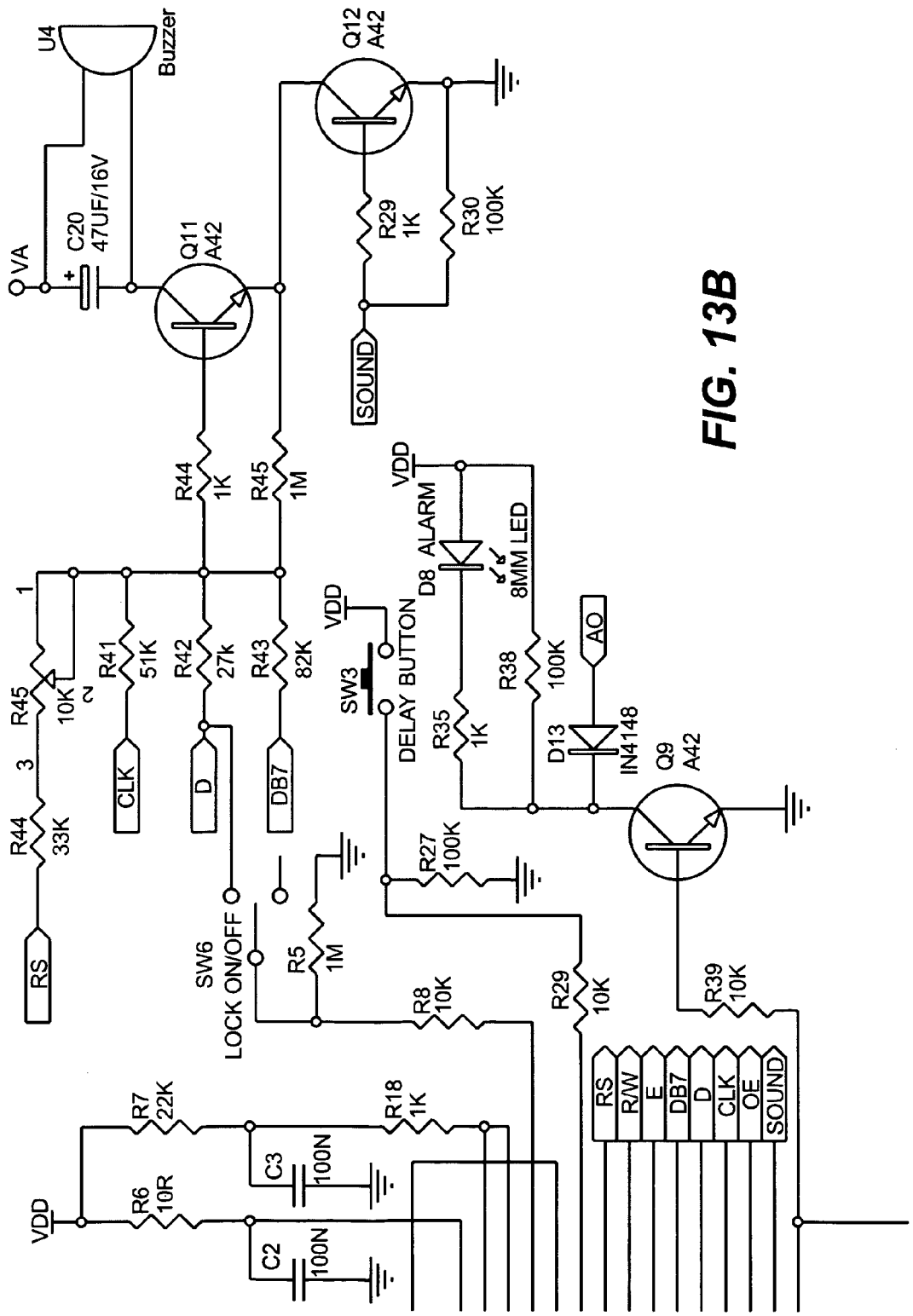
Figure 13C:
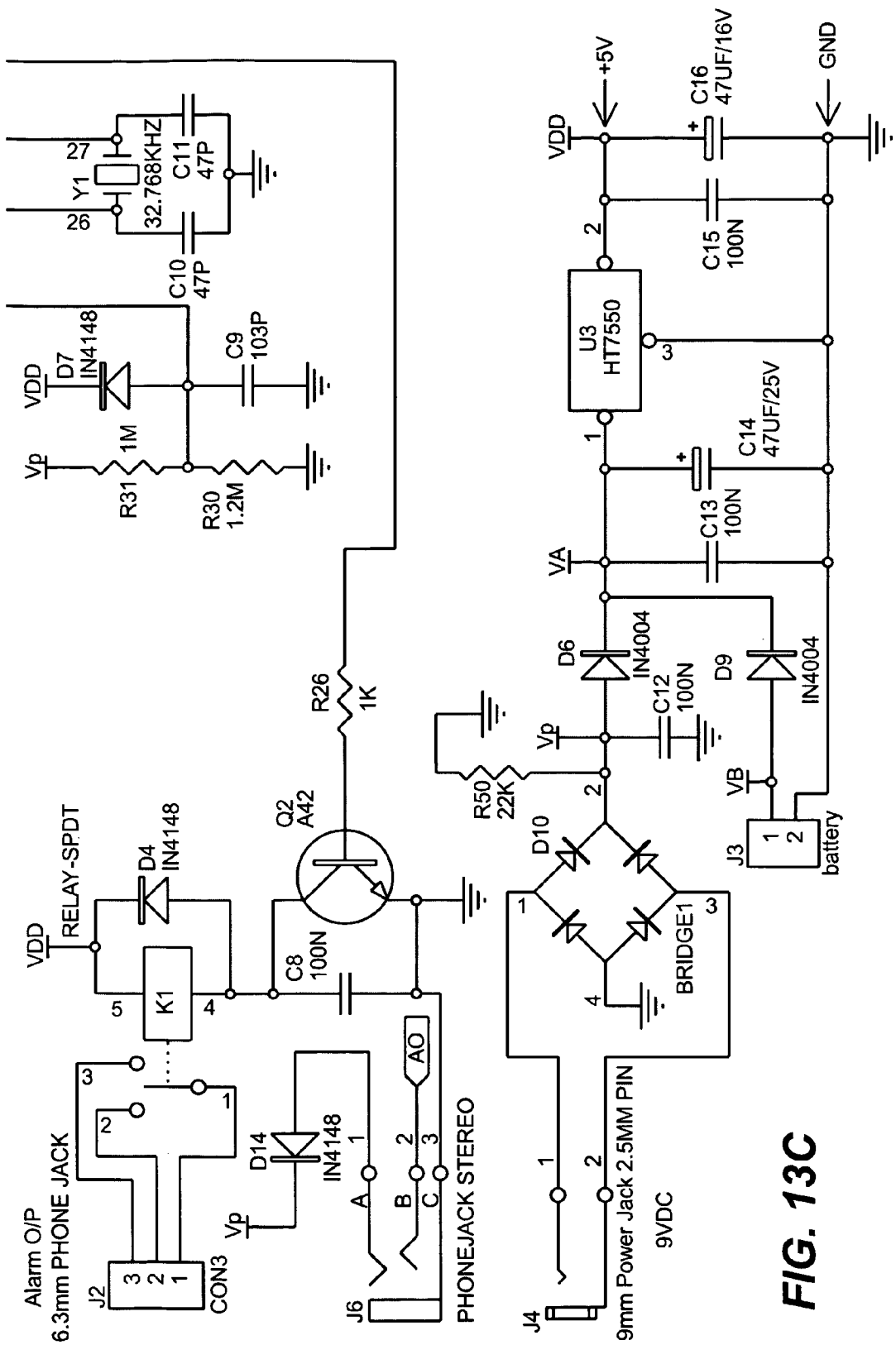
Figure 13D:
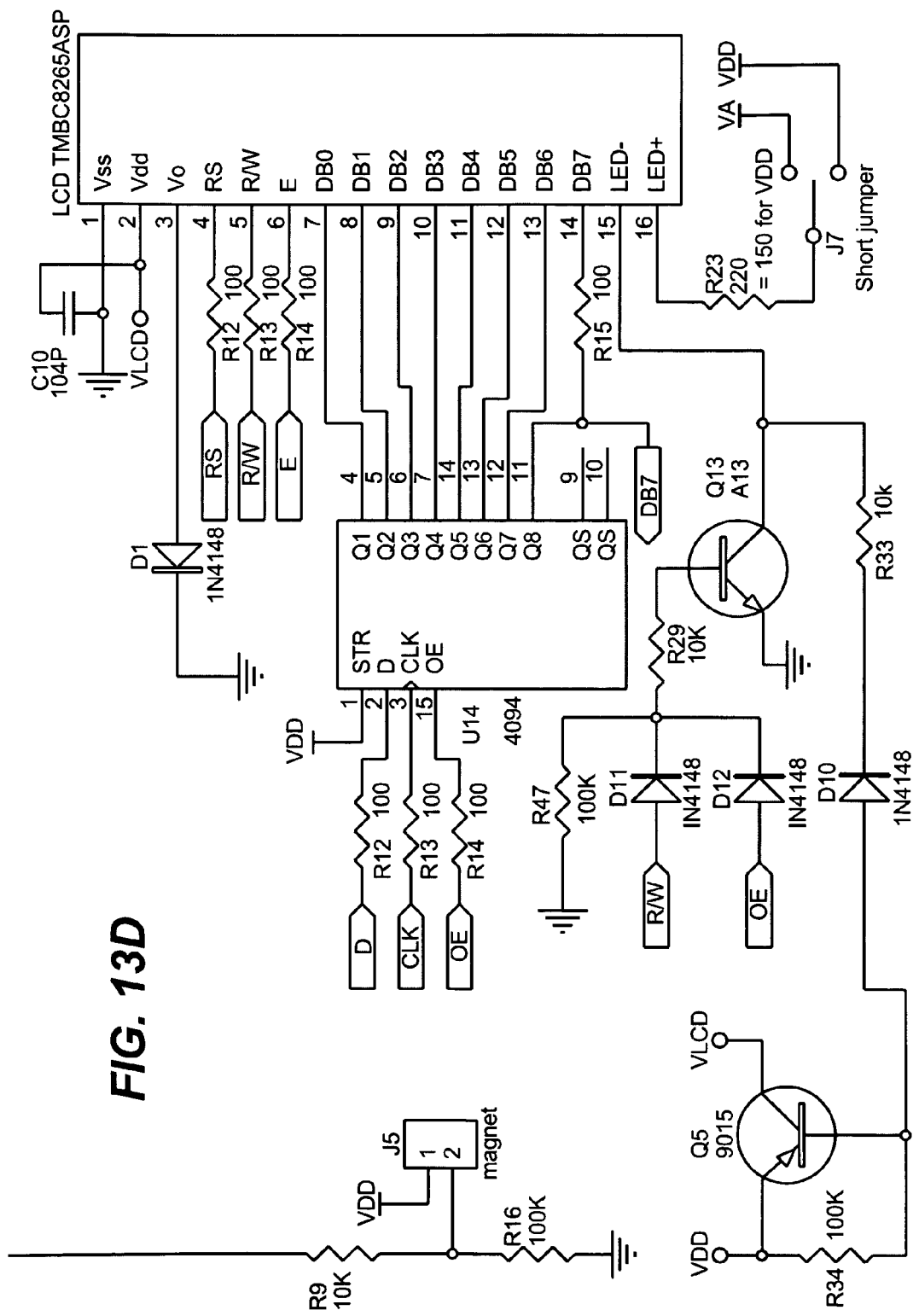

FIG. 10 is a circuit diagram of the wireless pad transmitter 1000, while FIG. 11 is a circuit diagram 1100 of the wireless bed pad receiver unit. FIG. 12 is a circuit diagram 1200 of the bed pad monitor of the present invention; and FIG. 13 is a circuit diagram 1300 of the wireless bad pad monitor having an LCD display.

Referring to FIG. 10, there is shown a schematic drawing of wireless pad transmitter 1000. is connected directly to a bed pad, and transmits the conditions of the bed pad to a proximate wireless bed pad receiver unit 1100. In this figure, it can be seen that microcontroller U2 is in communication with connector J1, which is externally connected to a bed pad's output port. Through this port, microcontroller U2 monitors the conditions of the pad. Microcontroller U2 is programmable via connector J2.

DC voltage (VDD) is provided to the circuits of wireless pad transmitter 1000 by way of 3.2 volt battery BT1. The output voltage of battery BT1 is regulated to 3.0 volts by voltage regulator U3. VDD is also passed through voltage regulator U1, whose output is monitored by the RA3 analog input on pin 2 of microcontroller U2. The software running on microcontroller U2 generates an alarm when VDD drops below a certain voltage (indicating a low battery condition).

Any alarms generated by microcontroller U2 are converted into formatted data messages that are then sent (via RB7 pin 13 of microcontroller U2) to the transmitter module connected to connector J3 (the data is passed on pin 3 of connector J3). The transmitter module connected to connector J3 receives these data messages and modulates the data onto the RF signal transmitted to the receiver module connected to a proximate bed pad monitor. In this way, the alarms generated by conditions detected by microcontroller U2 are sent wirelessly to a remote monitor. Microcontroller U2 also communicates with memory chip IC1. Memory chip IC1 is used to store data.

Referring now to FIG. 11, there is shown a schematic drawing of wireless bed pad receiver unit 1100. Wireless bed pad receiver unit 1100 is connected (via connector J1) to an input port of a non-wireless bed pad monitor, thereby making the monitor operate in a wireless mode. In this schematic, it can be seen that microcontroller U1 (via RB7 input pin 13) receives data from a RF receiver module via DATA pin 9 of connector J2. This is the path by which data transmitted by wireless pad transmitter(s) 1000 is passed to microcontroller U1.

Note that, through the receiver, microcontroller U1 can receive data from more than one wireless pad transmitter 1000. However, only data from those wireless pad transmitters that have been 'matched' to the specific instance of wireless bed pad receiver unit 1100 will be processed.

To 'match' a specific wireless pad transmitter 1000 to the specific instance of wireless bed pad receiver unit 1100, the user first presses 'LEARN MODE' momentary-on switch SW2. This causes RA3 pin 2 on microcontroller U1 to be pulled up from ground to VDD. The software running on microcontroller U1 detects this change, and begins running 'learn mode' routines that store (in memory chip IC1) data captured by the receiver module connected to connector J2. Microcontroller U1 then automatically 'matches' to (stores the unique transmitted code of) any wireless pad transmitter 1000 that is transmitting nearby. While wireless bed pad receiver unit 1100 is in this mode, one or more wireless pad transmitter 1000 can be triggered (by pressing on the pad itself) to transmit, and thereby be 'matched' to the specific instance of wireless bed pad receiver unit 1100. Wireless bed pad receiver unit 1100 is can be made to exit the learning mode by pressing 'LEARN MODE' momentary-on switch SW2 once again.

In FIG. 11 it can also be seen that wireless bed pad receiver unit 1100 receives +5V DC voltage (VDD) via pin 1 of connector J1. Connector J1 is externally connected to a monitor that analyzes and displays to received information to a user. VDD is regulated by voltage regulator U5 and then passed to the receiver module via transistor Q2, and then through pins 6 and 10 of connector J2. Transistor Q2 can be turned on and off by microcontroller U1 (via RB6 pin 12 of microcontroller U1). Turning off transistor Q2 causes the VDD to be removed from the receiver module.

Still referring to FIG. 11, it can be seen that microcontroller U1 passes information to the monitor attached to connector J1. The information provided to the monitor includes: on pin 2 of connector J1, a 'buzzer-on' condition, on pin 3 of connector J1, a 'RF signal lost' condition, on pin 4 of connector J1, a 'RF signal OK' condition, on pin 5 of connector J1, a 'bed pad' condition, on pin 6 of connector J1, a 'mat' condition, on pin 7 of connector J1, a 'low battery' condition.

Now referring to FIG. 12, a circuit diagram of wireless bed pad monitor 1200 is shown. It can be seen that wireless bed pad monitor 1200 is a bed monitor circuit integrated with the key elements of a bed pad receiver unit 1100. First, addressing the receiver portion of the schematic of FIG. 12, it can be seen that microcontroller U3 (via RB7 input pin 13) receives data from a RF receiver module via DATA pin 9 of connector J5. This is the path by which data transmitted by wireless pad transmitter(s) 1000 is/are passed to microcontroller U3. Note that, through the receiver, microcontroller U3 can receive data from more than one wireless pad transmitter 1000. However, only data from those wireless pad transmitters that have been 'matched' to the specific instance of wireless bed pad receiver unit 1100 will be processed.

To 'match' a specific wireless pad transmitter 1000 to the specific instance of wireless bed pad monitor 1200, the user first presses 'LEARN MODE' momentary-on switch S1. This causes RA3 pin 2 on microcontroller U3 to be pulled up from ground to VDD. The software running on microcontroller U3 detects this change, and begins running 'learn mode' routines that store (in memory chip IC1) data captured by the receiver module connected to connector J5. Microcontroller U3 then automatically 'matches' to (stores the unique transmitted code of) any wireless pad transmitter 1000 that is transmitting nearby. While wireless bed pad monitor 1200 is in this mode, one or more wireless pad transmitter 1000 can be triggered (by pressing on the pad itself) to transmit, and thereby be 'matched' to the specific instance of wireless bed pad monitor 1200. Wireless bed pad monitor 1200 is can be made to exit the learning mode by pressing 'LEARN MODE' momentary-on switch S1 once again.

In FIG. 12 it can also be seen that wireless bed pad monitor 1200 receives +5V DC voltage (VDD) from the output of voltage regulator U4. VDD is regulated by voltage regulator U5, and then passed to the receiver module via transistor Q4, and then through pins 6 and 10 of connector J2. Transistor Q4 can be turned on and off by microcontroller U3 (via RB6 pin 12 of microcontroller U3). Turning off transistor Q4 causes the VDD to be removed from the receiver module.

Still referring to FIG. 12, it can be seen that microcontroller U3 (via RA2 pin 1 of microcontroller U3) passes data to microcontroller U2 (via RA3 pin 2 of microcontroller U3). In this way microcontroller U2 receives bed pad alarm information that has been received by the receiver unit.

Microcontroller U3 performs the function of illuminating the Signal Lost LED4 and Signal OK LED3 based on the conditions of the radio frequency signals currently being seen by the receiver module attached to connector J5. Microcontroller U3 (via RB3 pin 9 of microcontroller U3) also controls the current flow through transistor Q2. Turning the current on through transistor Q2 activates buzzer BUZ1. Turning off the current through transistor Q2 deactivates buzzer BUZ1.

Microcontroller U3 (via RA0 pin 17 of microcontroller U3) outputs a MAT logical signal that indicates the condition of an attached mat (if a mat is attached). This MAT logical signal is passed to pin 4 of telephone jack connector J1. This MAT logical signal is also passed to RB0 pin 6 of microcontroller U3. In this manner, any conditions detected in data received by microcontroller U3 (from the receiver module connected to connector J5) are made available to both microcontroller U2 and to a wireless pad transmitter 1000 connected to wireless bed pad monitor 1200 via telephone jack connector J1. If a wireless pad transmitter 1000 is connected to wireless bed pad monitor 1200 via telephone jack connector J1, then the integrated system acts as a repeater, receiving transmitted messages from instances of wireless pad transmitter 1000, and then wirelessly transmitting those messages to a remote centralized wireless monitoring system. This approach is used when placing an instance of positioning a wireless bed pad monitor 1200 just over the door of each room on a nursing floor in a hospital. In this scenario, a centralized wireless monitor system is positioned at the nursing station. As a bed pad alarm is generated, the wireless bed pad monitor 1200 just over the door of the room in which that bed pad resides will display an alarm locally, and then re-transmit the message to the centralized monitor at the nurse station. In this way, the nurse at the station can see the alarm, and then proceed to deal with the issue immediately. Also, if a nurse is not at the nurse station, then the visible and audible alarm generated locally by wireless bed pad monitor 1200 will immediately guide the nurse to the bed from which the alarm was issued.

Still referring to FIG. 12, the functions of microcontroller U2 and its associated circuits are now described. It can be seen that DC voltage is provided to the module in one of two ways. First, battery power is provided to voltage regulator U4 via battery connector J6 and diode D6. Voltage regulator U4 provides +5V VDD as its output. The second power input is +9VDC or 9VAC from an external source via 9 mm power jack J4. This voltage is fed through bridge rectifier D2 (BRIDGE1) to the Vp source point, as well as to the input of voltage regulator U4 via diode D5. The input (pin 2) of voltage regulator U4 is also the source point for VA. VA serves as the voltage by which the battery condition is measured.

The battery condition is determined by having VA feed the input of voltage regulator U1, the output of which (when the unit is operating only on battery) provides the only voltage to input RA1 pin 18 of microcontroller U2. The software running on microcontroller U2 measures the regulated VA voltage and determines the battery condition based on this voltage. If the voltage drops below a predetermined value, then the software running on microcontroller U2 generates an alarm. It can be seen that microcontroller U2 can illuminate alarm indicators LED1 and LED2. It can also be seen that microcontroller U2 can generate an oscillating signal out through transistor Q1 and inductor L1 to connector J2. The output level of this signal is adjusted by way of variable resistor VR1. It can further be seen that microcontroller U2 can (via RB7 output pin 13 of microcontroller U2) operate the dry contacts of SPDT relay K1 via control of transistor Q3 (transistor Q3 activates and deactivates relay K1. Relay K1 provides a dry contact output for external systems use. This output can be either polarity, depending on which pins of connector J3 are used. The outputs described above are operated under the control of the software running on microcontroller U2. This software also regularly examines the condition of momentary-on reset button SW2, as well as the condition of magnetic switch SW3 via RA0 input pin 17 of microcontroller U2. If magnetic switch SW3 closes, the software interprets this as a reset command, and as long as switch SW3 remains closed, no action is taken. If reset button SW2 is pressed (and reset on//off switch SW1 is set to 'ON') the software interprets this as a reset, and clears its alarms.

Additionally, the software running on microcontroller U2 monitors the condition of inputs RB1 (pin 7), RB2 (pin 8) and RB3 (pin 9) to determine the tone setting established by the position of tone selector switch SW4.

Now referring to FIG. 13, a circuit diagram of (a non-wireless) bed pad monitor 1300 with an LCD display is shown. It can be seen that bed pad monitor 1300 received bed pad conditions through telephone jack connector J1 (which is connected directly to the output port of a bed pad). The microcontroller U2 receives the inputs present on connector J1 as pad condition (at RA2 pin 8 of microcontroller U2, mat condition (at RB0 pin 10 of microcontroller U2 and other condition (at RC1 pin 19 of microcontroller U2). In this arrangement, microcontroller U2 can detect and analyze each of these conditions.

Microcontroller U2 also regularly monitors the condition of momentary-on delay switch SW3. If this button is pressed, microcontroller U2 ignores external inputs for a period of time, and therefore, during that time, will not generate alarms. Microcontroller U2 also regularly monitors the condition of momentary-on switch SW3.

Still referring to FIG. 13, it can be seen that microcontroller U2 controls the displayed image of the LCD display by shifting data serially into logic translator U14. Logic translator U14 then translates the serial input into a parallel output to the LCD display. In this way, microcontroller U2 can display messages on the LCD display. Microcontroller U2 can also operate buzzer U4 and alarm LED D8.

In addition to the LCD display, microcontroller U2 controls other outputs, including dry contact relay K1. In the configuration shown in FIG. 13, microcontroller U2 detects (via telephone jack connector J1) the locally connected bed pad's conditions, and then displays those conditions on the LCD display, as well as providing audible and visible alarm indications.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:

1. A patient monitoring system, comprising:
   a bed pad monitor having a bed pad monitor receiver and an alarm; and
   a pressure pad having a pressure pad transmitter in wireless RF communication with said bed pad monitor receiver;
   wherein said pressure pad transmitter sends a wireless signal to said bed pad monitor receiver to indicate to a caregiver that a patient has gotten out of, or fallen out of, a bed or a chair, and further wherein said bed pad transmitter sends a coded pulsed signal to said bed pad monitor receiver, such that if said bed pad monitor receiver misses a pulsed signal from said pressure pad transmitter over a predetermined and preset period, it will output an alarm signal indicating that said pressure pad is lost or removed.

2. The system of claim 1, wherein said pressure pad includes a uniquely coded chip for matching said pressure pad with said bed pad monitor, and wherein said pressure pad is matched to said bed pad monitor by pressing a read in button on said bed pad monitor and then pressing said pressure pad to match the codes automatically.

3. The system of claim 2, wherein said wireless RF signal includes a checksum to prevent faulty data.

4. The system of claim 1, further including a plurality of pressure pads matched to at least one bed pad monitor.

5. The system of claim 1, wherein said bed pad monitor includes an LCD controller and an LCD visual display, a receiver controller having an autoread button and EEPROM for reading pad transmitter information into memory, a receiver module, a low battery detect circuit, an audible output speaker, a switch for controlling inputs, and an LED/relay control/data output circuit portion.

6. The system of claim 1, wherein said bed pad transmitter comprises a microcontroller having a buffer, EEPROM for storing programmed inputs from a keypad or other input device, a low battery detect circuit, an antenna, and a multi-frequency hopping option for sending a wideband frequency hopping signal to said bed pad monitor receiver.

7. The system of claim 1, wherein said bed pad monitor receiver comprises a microcontroller having a low power receiver module, EEPROM, a low battery detector, an LED indicator with indications for Pad OK, Status, and Low Battery, and an audible output device.

8. The system of claim 7, wherein said system includes a plurality of pressure pads, a plurality of bed pad monitors, and wherein each of said bed pad monitors includes an autoread button for matching that bed pad monitor to at least one of said pressure pads.

9. The system of claim 1, further including a central bed monitor receiving and alarm unit, and wherein said bed pad monitor receiver includes a transmitter programmed to relay signals from said pressure pad to said central bed monitor receiving and alarm unit.

10. The system of claim 1, wherein said pressure pad transmitter sends a coded signal matched with a particular bed pad monitor receiver.

11. The system of claim 10, wherein said coded signal is sent outside the patient's room directly to said bed pad monitor receiver, such that an alarm output alerts caregivers to take appropriate action.

* * * * *